United States Patent
Han et al.

(10) Patent No.: US 11,209,510 B2
(45) Date of Patent: Dec. 28, 2021

(54) UNIFIED COIL (UNIC) SYSTEMS AND METHOD FOR NEXT GENERATION MAGNETIC RESONANCE COILS

(71) Applicant: Cedars-Sinai Medical Center, Los Angeles, CA (US)

(72) Inventors: Hui Han, West Hollywood, CA (US); Debiao Li, South Pasadena, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 587 days.

(21) Appl. No.: 15/763,383

(22) PCT Filed: Nov. 3, 2016

(86) PCT No.: PCT/US2016/060403
§ 371 (c)(1),
(2) Date: Mar. 26, 2018

(87) PCT Pub. No.: WO2017/079487
PCT Pub. Date: May 11, 2017

(65) Prior Publication Data
US 2018/0275234 A1  Sep. 27, 2018

Related U.S. Application Data

(60) Provisional application No. 62/252,031, filed on Nov. 6, 2015.

(51) Int. Cl.
*G01R 33/3875* (2006.01)
*A61B 5/00* (2006.01)
(Continued)

(52) U.S. Cl.
CPC ........ *G01R 33/3875* (2013.01); *A61B 5/0042* (2013.01); *A61B 5/0044* (2013.01);
(Continued)

(58) Field of Classification Search
CPC ............ G01R 33/3875; G01R 33/3415; G01R 33/34046; G01R 33/341; A61B 5/055;
(Continued)

(56) References Cited

U.S. PATENT DOCUMENTS

| 5,349,297 A | 9/1994 | DeMeester et al. |
| 5,773,976 A | 6/1998 | Sakakura et al. |

(Continued)

FOREIGN PATENT DOCUMENTS

| CN | 101452065 A | 6/2009 |
| CN | 103424723 A | 9/2013 |

(Continued)

OTHER PUBLICATIONS

International Search Report and Written Opinion of PCT/US2016/060403 dated Jan. 30, 2017, 9 Pages.
(Continued)

*Primary Examiner* — Son T Le
*Assistant Examiner* — Dustin R Dickinson

(57) ABSTRACT

A unified coil assembly for magnetic resonance imaging is disclosed. The coil assembly includes an RF coil element and a shim coil array with a shim coil element. The shim coil element is physically separated or partially separated from the RF coil element. The shim coil element includes a DC current loop having a DC power supply connection to allow DC current to generate a local B0 magnetic field. The unified coil array assembly is configured to simultaneously provide an RF mode for at least one of transmit or receive and a direct current mode to generate a local B0 magnetic field for B0 shimming Larger number of shim coils relative to the RF coil element provides superior shimming performance. The mutual inductance between the shim coil element and the RF coil element is minimized by proposed
(Continued)

geometrical decoupling methods in order to minimize the RF interaction between the two.

33 Claims, 13 Drawing Sheets

(51) Int. Cl.
    *A61B 5/055*     (2006.01)
    *G01R 33/3415*     (2006.01)
    *G01R 33/341*     (2006.01)
    *G01R 33/34*     (2006.01)

(52) U.S. Cl.
    CPC ............ *A61B 5/055* (2013.01); *A61B 5/4312* (2013.01); *A61B 5/459* (2013.01); *A61B 5/4566* (2013.01); *A61B 5/4585* (2013.01); *A61B 5/4595* (2013.01); *G01R 33/341* (2013.01); *G01R 33/3415* (2013.01); *G01R 33/34046* (2013.01)

(58) Field of Classification Search
    CPC ... A61B 5/0042; A61B 5/0044; A61B 5/4312; A61B 5/4566; A61B 5/4585; A61B 5/459; A61B 5/4595
    See application file for complete search history.

(56) References Cited

U.S. PATENT DOCUMENTS

| | | | |
|---|---|---|---|
| 6,630,829 B1 | 10/2003 | Liu | |
| 7,323,875 B2 | 1/2008 | Ni et al. | |
| 7,414,401 B1 | 8/2008 | Lvovsky | |
| 7,598,739 B2 | 10/2009 | Vaughan, Jr. et al. | |
| 7,714,580 B2 | 5/2010 | Kruip | |
| 7,777,489 B2 | 8/2010 | Kawamoto | |
| 8,536,870 B2 | 9/2013 | Punchard et al. | |
| 8,704,516 B2 | 4/2014 | Van Den Brink et al. | |
| 8,981,779 B2 | 3/2015 | Shvartsman et al. | |
| 8,994,373 B2 | 3/2015 | Stemmer | |
| 2007/0282194 A1 | 12/2007 | Wiggins et al. | |
| 2008/0129298 A1 | 6/2008 | Vaughan et al. | |
| 2010/0002926 A1* | 1/2010 | Dahnke | G01R 33/5601 382/131 |
| 2010/0317961 A1* | 12/2010 | Jenkins | A61B 5/053 600/411 |
| 2011/0037467 A1* | 2/2011 | Tsuda | G01R 33/3806 324/309 |
| 2012/0249137 A1* | 10/2012 | Witschey | G01R 33/3875 324/309 |
| 2012/0274326 A1 | 11/2012 | Lee et al. | |
| 2014/0002084 A1 | 1/2014 | Han et al. | |
| 2015/0061676 A1* | 3/2015 | Hocht | G01R 33/341 324/318 |
| 2015/0185300 A1 | 7/2015 | Shvartsman et al. | |
| 2015/0323628 A1 | 11/2015 | Wald et al. | |

FOREIGN PATENT DOCUMENTS

| | | |
|---|---|---|
| CN | 104471421 A | 3/2015 |
| JP | 2005013702 A | 1/2005 |
| WO | 2017079487 A1 | 5/2017 |

OTHER PUBLICATIONS

Juchem et al., Multicoil Shimming of the Mouse Brain, 2011, Magnetic Resonance in Medicine, vol. 66, pp. 893-900.
Extended European Search Report for Application No. EP 16863005.1, dated May 31, 2019 (13 pages).
Darnell D. el al.; "Integrated parallel reception, excitation, and shimming (IPRES) with split DC loops for improved B0 shimming"; Proceedings of the International Society for Magnetic Resonance in Medicine, ISMRM, 23rd Annual Meeting and Exhibition, Toronto, Ontario, Canada, May 30-Jun. 5, 2015, No. 861, p. 861; May 15, 2015; XP040666541.
NIH-PA Author Manuscript; Christopher Juchem et al., "Magnetic field modeling with a set of individual localized coils"; J Magn Reson. Jun. 2010; 204(2): 281-289.

* cited by examiner

UNIFIED COIL (UNIC) SYSTEMS AND METHOD FOR NEXT GENERATION MAGNETIC RESONANCE COILS

CROSS-REFERENCE TO RELATED APPLICATIONS

This application is a National Phase of International Application No. PCT/US6/060403 filed Nov. 3, 2016, which designated the U.S. and that International Application was published under PCT Article 21(2) in English, which also includes a claim of priority under 35 U.S.C. §119(e) to U.S. Provisional Patent Application No. 62/252,031 filed Nov. 6, 2015, the entirety of which is hereby incorporated by reference.

TECHNICAL FIELD

The present disclosure relates to systems and methods for magnetic resonance imaging. More specifically, the present disclosure relates to a unified coil (UNIC) system consisting of separate or partially shared-conductor RF and shim coil arrays.

BACKGROUND

During the past few decades, major developments in magnetic resonance imaging (MRI) scanner technology have been driven by the ever-increasing demand for higher static magnetic field (B0) strengths, prevalently 1.5 Tesla a decade ago, now 3 Tesla, and in the future probably 7 Tesla. As is understood, MRI uses such powerful magnets to generate a magnetic field over the area of scanning interest. An MRI scanner uses a radio frequency (RF) coil or coil array that generates radio frequency (RF) waves into the area of interest. A transmitting RF coil is used to generate the RF magnetic field and a receiver RF coil is used to receive RF signals from the area of interest that indicate the composition of the tissue. The static magnetic field (B0) inhomogeneity has always been one major challenge with increased field strengths. Another major challenge is the inhomogeneity of the radio frequency (RF) magnetic field (B1). Many off-resonance imaging problems are essentially attributed to B0 field inhomogeneities, which are unfortunately proportional to the B0 field strength. For example, image artifacts and signal voids compromise whole brain functional imaging particularly in prefrontal cortex and temporal cortex and cardiac SSFP imaging particularly at 3 Tesla and higher field strengths. The shimming magnetic field is used to adjust the homogeneity of the static magnetic field (B0) and therefore remedy the inhomogeneity of the RF magnetic field (B1).

The RF coils in current scanner designs are placed in proximity to the area of interest. For example the magnet to generate the static magnetic field may be located in a tube around a patient, while the RF coil is located nearer to the chest of the patient in the tube. The shimming coil is currently located in the tube but is generally inefficient because it is too far removed from the RF coil.

Since 2012, a new platform MR coil technology, known as an "iPRES" coil, has been proposed to solve the challenge of the inhomogeneities of the static magnetic field (B0). "iPRES" is defined as integrated, parallel, reception, excitation, and shimming. The iPRES coil system is an integrated RF and B0 shimming coil array. Such a system is described in U.S. Patent Publication No. 2014/0002084 to inventors Hui Han, Trong-Kha Truong, and Allen Song at the Duke University Medical Center.

The iPRES concept uses a single coil array rather than separate coil arrays for parallel RF reception/transmission and B0 field shimming. It relies on a circuit design that allows a radio frequency current for excitation/reception and a direct current for B0 shimming to coexist independently in the same physical coil loop or conductor. The underlying principle that currents or waves at different frequencies can coexist independently in the same conductor or media without undesired interference between them is simple and widespread in the electro-physics and communications fields.

The iPRES system has now been regarded as probably the most efficient and easy to implement shimming technology compared to all other existing shimming techniques including in-scanner spherical harmonic (SH) shim coils, multi-coil shimming techniques using separate shim coils/elements distantly located from an RF coil array. The localized multi-coil shimming functionality inherently provided by the same RF/DC coil loops can address many off-resonance imaging problems due to air/bone/tissue susceptibility differences in brain, cardiac, and musculoskeletal imaging at an unprecedented level, thus greatly increasing image fidelity and resolution in problematic regions of interest. The iPRES technology may be applied to a range of coils from head coils, cardiac coils, musculoskeletal coils, breast coils, knee coils, and etc. Such integrated RF/shim arrays will likely replace current generation RF coil array with minimal modification of MRI system hardware architecture.

Although largely surpassing other existing technologies, there are still two critical limitations inherent in iPRES coils, particularly for 3 T & 1.5 T human body MRI scanners, prevalent in most hospitals and research institutes, and all animal MRI scanners. First, the size, shape, and position of the DC shim loops are limited to the same as the RF loops because both RF and DC currents flow in the same conductor/loop. Second, the number of DC shim coil loops for an iPRES coil is limited by the number of available RF receivers, i.e., 32 RF receivers (with 32 shim coils) in state-of-the-art 3 T human body scanners and 16 or 8 RF receivers (with 16 or 8 shim coils) in many 1.5 T/3 T scanners, and 1-8 RF receivers (with 1-8 shim coils) in most animal scanners. Another problem with iPRES coils is the need for multiple large-size RF chokes in order to suppress unwanted RF currents generated in the DC shim coil loop.

These limitations largely constrain the effectiveness of shimming that prevents increasing the number of shim coils. Increasing the number of shim coils (i.e., the number of freedoms) can dramatically improve shimming effectiveness. Equally important, the size of the shim coils should match the dimension of anatomical structures possessing high-order (above second order) field inhomogeneities due to air/bone/tissue susceptibility differences, in order to generate opposite high-order shim fields to cancel the inhomogeneous field within those anatomical structures. In addition, the increasing number of large-size RF chokes increases coil construction complexity and degrades RF coil performance due to their interaction with RF fields.

Thus, there is a need for a magnetic resonance coil system that allows for more shim coils than the number of RF receiver channels to improve shimming effectiveness. There is also a need for a coil system that allows separate RF and shim loop arrays that overlap and share the same surface or layer of a coil mechanical supporting structure with a minimal distance between them to improve shimming effectiveness. There is also a need for a coil system that does not require the increase of the radial diameter of a MRI RF coil compared to a conventional RF array or coil or an iPRES coil or an oPRES array. There is also a need for a coil assembly that minimizes the number of RF chokes required in the shimming coil. More importantly, there is a need for a coil system that minimizes the interaction between the shimming coils and the RF coil array due to their mutual inductance.

SUMMARY

One example is a Magnetic Resonance Imaging (MRI) system that includes a mechanical coil supporting structure and a united coil array system. The unified coil array system includes an RF coil array having a plurality of coil elements. Each of the coil elements are operative in an RF mode for at least one of transmit or receive. A separate shim coil array has a plurality of coil elements operative in a direct current (DC) mode with DC current flow in the respective coil elements generating local B0 magnetic fields for B0 shimming. The two separate RF and shim coil arrays are geometrically overlapped and share the same surface or layer of the mechanical coil supporting structure. The two separate RF and shim coil arrays are inherently RF decoupled from each other by geometrical decoupling methods to minimize the RF interactions between two coil systems. A magnet bore of a MRI scanner holds a target object. The mechanical structure supports the separate RF coil and shim arrays to be positioned about the target object. A DC power supply is in communication with the shim coil array to supply DC current to the respective coil elements of the shim coil array. A shim coil circuit is in communication with the shim coil array configured to direct the DC power supply to supply the DC current to the respective coil elements to generate the local B0 magnetic fields for B0 shimming. An RF circuit is in communication with the separate RF coil array configured to receive an MR signal from the object for RF receive or transmit RF pulses to the object for RF transmit.

Another example is a Magnetic Resonance Imaging (MRI) system that includes a mechanical coil supporting structure and a united coil array system. The unified coil array system includes an RF coil array having a plurality of coil elements. Each of the coil elements are operative in an RF mode for at least one of transmit or receive. A shim coil array has a plurality of coil elements operative in a direct current (DC) mode with DC current flow in the respective coil elements to generate local B0 magnetic fields for B0 shimming. The RF and shim coil arrays share at least one physical conductor, and are geometrically overlapped and share the same surface or layer of the supporting structure. The two separate RF and shim coil arrays are inherently RF decoupled from each other by geometrical decoupling methods to minimize the RF interactions between two coil systems. A magnet bore of a MRI scanner holds a target object. The mechanical structure supports the separate RF coil and shim arrays to be positioned about the target object. A DC power supply is in communication with the shim coil array to supply DC current to the respective coil elements of the shim coil array. A shim coil circuit is in communication with the shim coil array configured to direct the DC power supply to supply the DC current to the respective coil elements to generate the local B0 magnetic fields for B0 shimming. An RF circuit is in communication with the separate RF coil array configured to receive an MR signal from the object for RF receive or transmit RF pulses to the object for RF transmit.

Another example is a method of shimming Magnetic Resonance (MR) systems. At least one shim coil array with a plurality of coil elements is provided. The coil elements have associated circuits with a direct current (DC) current path comprising at least one loop. The at least one RF coil array is operated in at least one of an RF transmit or receive mode. The RF coil array is separate from the at least one shim coil array. The two separate RF and shim coil arrays are geometrically overlapped and share the same surface or layer of the mechanical coil supporting structure. The two separate RF and shim coil arrays are inherently RF decoupled from each other by geometrical decoupling methods to minimize the RF interactions between two coil systems. DC current is flowed through the DC current paths of the coil elements of at least one shim coil array concurrently with the transmit or receive mode of at least one RF coil array. Local B0 magnetic fields are generated in response to the flow of the DC current through the DC current paths of the coil elements, thereby B0 shimming an imaging space of a magnet of the MR system using the generated local B0 magnetic fields.

Another example is a method of shimming Magnetic Resonance (MR) systems. At least one shim coil array with a plurality of coil elements is provided. The coil elements have associated circuits with a direct current (DC) current path comprising at least one loop. The at least one RF coil array is operated in at least one of an RF transmit or receive mode and the RF and shim coil arrays share at least one physical conductor. The two separate RF and shim coil arrays are inherently RF decoupled from each other by geometrical decoupling methods to minimize the RF interactions between two coil systems. DC current is flowed through the DC current paths of the coil elements of at least one shim coil array concurrently with the transmit or receive mode of at least one RF coil array. Local B0 magnetic fields are generated in response to the flow of the DC current through the DC current paths of the coil elements, thereby B0 shimming an imaging space of a magnet of the MR system using the generated local B0 magnetic fields.

Another example is a unified coil array assembly for a Magnetic Resonance Imaging (MRI) system including a mechanical coil supporting structure, an RF coil and at least one shim coil array with a plurality of coil elements, each physically separated from the RF coil. The two separate RF and shim coil arrays are geometrically overlapped and share the same surface or layer of the mechanical coil supporting structure. The two separate RF and shim coil arrays are inherently RF decoupled from each other by geometrical decoupling methods to minimize the RF interactions between two coil systems. Each coil element includes a DC current loop having a DC power supply connection with positive and negative terminals. DC current flows and circulates in the DC current loop to generate a local B0 magnetic field. The unified coil array assembly is configured to simultaneously provide an RF mode for at least one of transmit or receive and a direct current mode to generate a local B0 magnetic field for B0 shimming.

Another example is a unified coil array assembly for a Magnetic Resonance Imaging (MRI) system including an RF coil and at least one shim coil array with a plurality of coil elements. At least one of the coil elements has a segment shared with the RF coil and a segment not shared with the RF coil. Each coil element includes a DC current loop having a DC power supply connection with positive and negative terminals. DC current flows and circulates in the DC current loop to generate a local B0 magnetic field. The unified coil array assembly is configured to simultaneously provide an RF mode for at least one of transmit or receive and a direct current mode to generate a local B0 magnetic field for B0 shimming. The two separate RF and shim coil arrays are inherently RF decoupled from each other by geometrical decoupling methods to minimize the RF interactions between two coil systems.

Additional aspects of the invention will be apparent to those of ordinary skill in the art in view of the detailed description of various embodiments, which is made with reference to the drawings, a brief description of which is provided below.

BRIEF DESCRIPTION OF FIGURES

Exemplary embodiments are illustrated in referenced figures. It is intended that the embodiments and figures disclosed herein are to be considered illustrative rather than restrictive.

FIG. 12 is a circuit diagram of a united coil array that has a partially overlapped but separated RF and DC shim loops;

DETAILED DESCRIPTION

Figure 1:
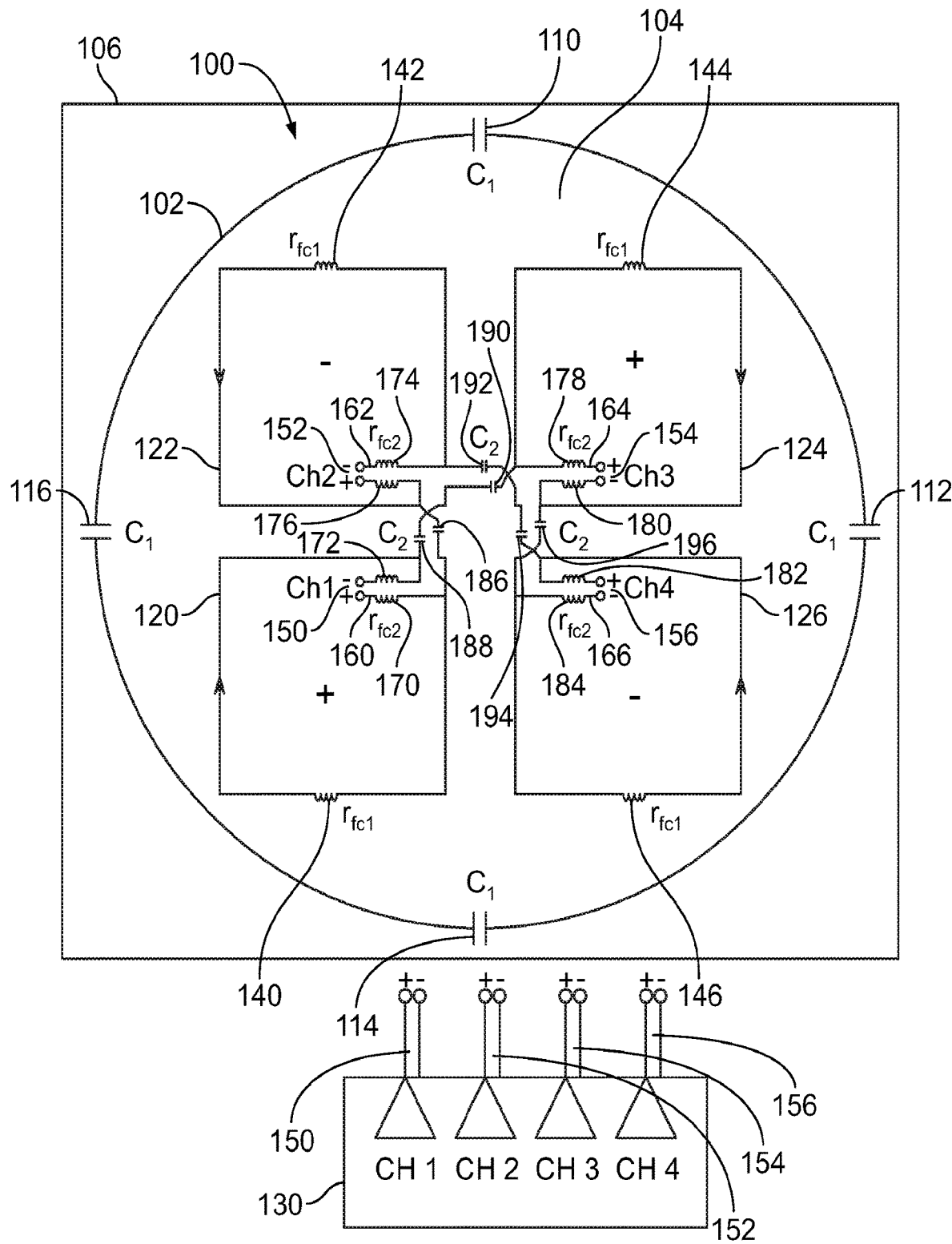
FIG. 1 is a circuit diagram of an example element design of a coil assembly with a separated RF coil and a shimming coil array.

FIG. 1 is a block diagram of a coil assembly 100 that includes a RF coil 102 and a shim array 104 for a magnetic resonance system. The RF coil 102 is an outer circular shaped loop that represents a traditional RF-only loop coil. In a previous system, the loop coil by definition either receives MR radiofrequency (RF) signals as a receive-only RF coil from the spins in tissue or non-tissue material, or transmits RF pulses as a transmit-only RF coil to excite the spins in tissue or non-tissue material, or performs both functions as a transmit and receive RF coil. The coil 102 includes a number of distributed capacitors 110, 112, 114, and 116 that stabilize the performance of the coil 102. The number of capacitors such as the capacitors 110, 112, 114, and 116 is n, a positive integer. In this example, n=4. In this example and other examples in this specification, a traditional RF-only loop coil will follow the same definition. The RF coil 102 and the shim array 104 are mounted on a coil supporting structure 106. The coil mechanical supporting structure 106 may be a coil helmet, coil housing, or any other mechanical coil assembly.

In this example, the diameter of the loop of the RF coil 102 may be between 2 cm and 30 cm depending on the application. For example, a cardiac coil array may include 16 loops, each being 10-20 cm in diameter, on a top chest structure and 16 loops, each being 10-20 cm in diameter, on a bottom chest structure. A head coil may have 32 loops, each having a diameter of 5-12 cm. Of course other sized loops and number of loops may be used for different types of arrays. The typical frequency for the RF signal may be 63.9 MHz or 63.6 MHz for a 1.5 T scanner, 128 MHz or 123.2 MHz for a 3 T scanner, and 298 MHz for a 7 T scanner.

The shim array 104 includes four interconnected identical square-shaped shim coils 120, 122, 124, and 126 that represent an example of the completely separate shim coil array 104 in relation to the RF coil 102. Both the RF coil 102 and the shim coils 120, 122, 124, and 126 are a conductor material. The shim coil array 104 in FIG. 1 is a four channel shim coil array with the DC current of each shim coil 120, 122, 124, and 126 independently controlled by a controller 130. In this example, the controller 130 is a four-channel DC current source that includes source amplifiers that provides a DC current supply. Each shim coil 120, 122, 124, and 126 is a square loop that has n distributed RF chokes where n may be 0 or a positive integer. In this example, each square loop of the respective coils 120, 122, 124, and 126 has a respective RF choke 140, 142, 144, and 146 that are each inductors. Other forms of local RF choke circuits such as an inductor in parallel with a capacitor, or any combination of inductors and/or capacitors and/or diodes may be used. The RF chokes 140, 142, 144, and 146 prevent RF currents but allow DC currents in the shim loops 120, 122, 124, and 126.

The shim coil array 104 thus includes four channels for each of the shim coil 120, 122, 124, and 126 that are each controlled by the controller 130. The channels Ch1+−, Ch2+−, Ch3+−, and Ch4+− in FIG. 1 represent the positive and negative polarities of DC current feeding terminals 150, 152, 154, and 156 of the 4-channel DC current source supply of the controller 130. The DC current for each shim coil 120, 122, 124, and 126 is independently controlled by each channel current amplifier in the controller 130 via respective pairs of DC feed wires 160, 162, 164, and 166. The current is controlled to all of the shim coils 120, 122, 124, and 126 via the controller 130 for a combined shim field. One or more RF chokes such as the RF chokes 170, 172, 174, 176, 178, 180, 182, and 184 are inserted in the DC feed wires 160, 162, 164, and 166 to eliminate unwanted RF currents. The RF chokes 170, 172, 174, 176, 178, 180, 182, and 184 are inductors in this example, but may be other types of local RF choke circuits for preventing RF currents but allowing DC currents. Each pair of DC feeding wires 160, 162, 164, and 166 are twisted together to avoid generating unwanted additional local magnetic fields.

The four identically sized square shim loops of the coils 120, 122, 124, and 126 are connected through three pairs of DC blocking capacitors 186, 188, 190, 192, 194, and 196. The positive terminal of the DC feed wire 160 is coupled to the shim coil 120 and the blocking capacitor 186. The other side of the blocking capacitor 186 is also coupled to the positive feed wire of the DC feed wire 162 and the shim coil 122. The negative terminal of the DC feed wire 160 is coupled to the shim coil 120 and the blocking capacitor 188. The other side of the blocking capacitor 188 is coupled to the blocking capacitor 190. The other side of the blocking capacitor 190 is coupled to the positive terminal of the DC feed wire 164 and the shim coil 124. The negative terminal of the DC feed wire 162 is coupled to the shim coil 122 and the blocking capacitor 192. The other side of the blocking capacitor 192 is also coupled to one side of the blocking capacitor 194. The other side of the blocking capacitor 194 is coupled to the positive feed wire of the DC feed wire 166 and the shim coil 126. The negative terminal of the DC feed wire 164 is coupled to the shim coil 124 and the blocking capacitor 196. The other side of the blocking capacitor 196 is coupled to the negative feed wire of the DC feed wire 166 and the shim coil 126. In this example, the capacitors 186, 188, 190, 192, 194, and 196 are between 0-10,000 PF. It is to be understood that the two blocking capacitors 188 and 190 may be replaced by a single capacitor and similarly the two blocking capacitors 192 and 194 may be replaced by a single capacitor.

As shown in FIG. 1, the four shim coils 120, 122, 124, and 126 are arranged symmetrically and routed sequentially in such a way that undesirable RF currents induced by the loop of the RF coil 102 will flow along the path directed by the arrows on the shimming coils 120, 122, 124, and 126. Therefore, the magnetic flux generated by unwanted RF currents have opposite signs (marks +– in FIG. 1) in each pair of two adjacent shim loops and thus cancel each other. For example, the loops 120 and 124 are positive flux while the loops 122 and 126 are negative flux. The mutual inductance between the shim coil array 104 and the RF coil 102 is zero and the shim coil array 104 is thus inherently decoupled from the RF coil 102. The geometrical symmetry of the shim coils 120, 122, 124, and 126 ensures that the direction of undesirable RF currents induced by the RF-only loop is clockwise in the shim coils 120 and 124 and is counterclockwise in the shim coils 122 and 126. Alternatively, if the direction of the undesirable current is counterclockwise in the shim coils 120 and 124, the direction is clockwise in the shim coils 122 and 126. As a result, the magnetic flux generated by the undesirable RF currents has opposite polarities in the shim coils 120 and 122 and 124 and 126, respectively.

Figure 2:
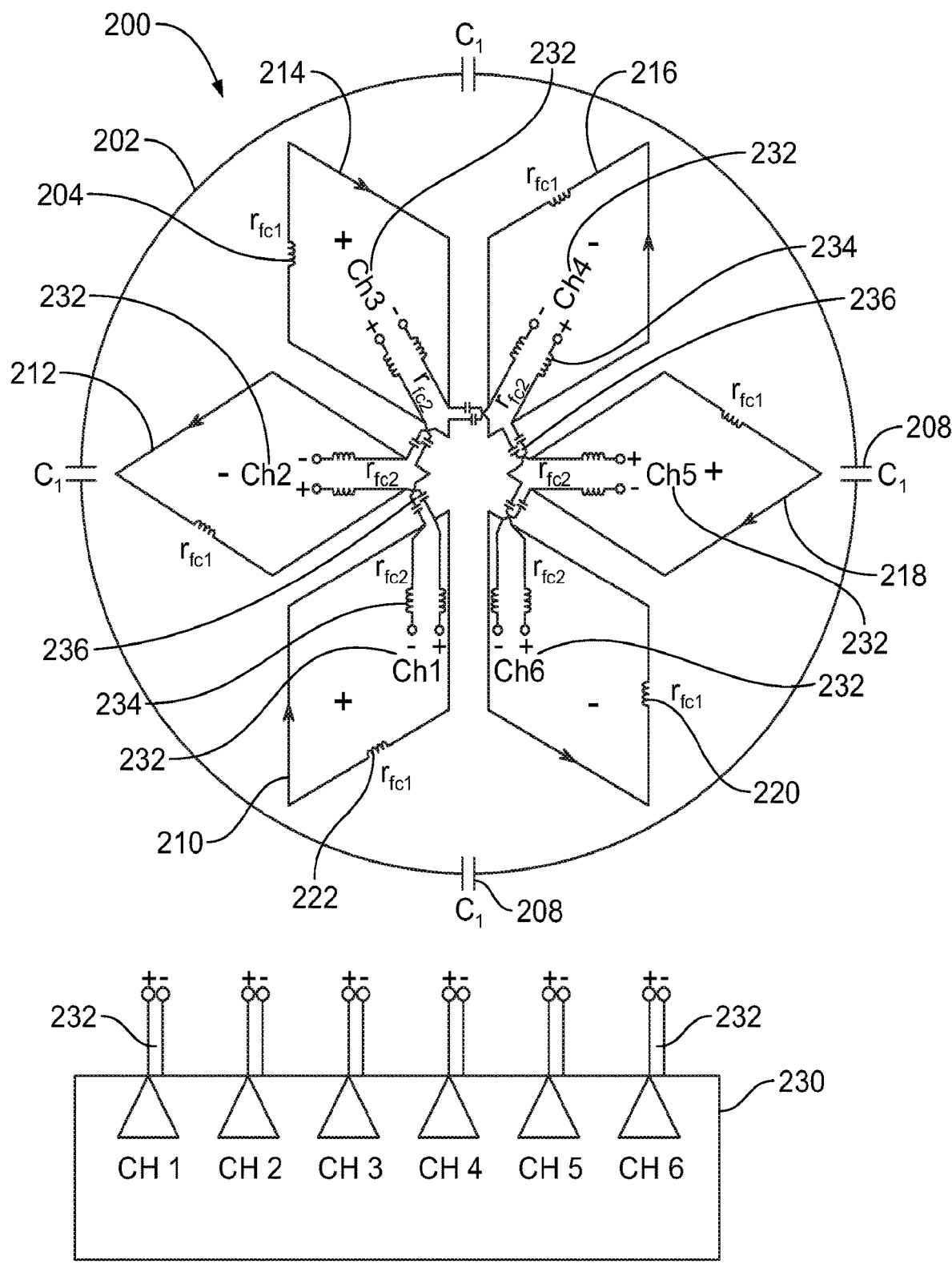
FIG. 2 is a circuit diagram of an example element design of a coil assembly with a separated RF coil and a shimming coil array with six coils.

Each shim loop and the RF loop may be a closed curve shape, a polygon shape, a square shape, a circular shape, a rectangular shape, a diamond shape, a triangular shape, or any other shape. FIG. 2 shows an alternate magnetic resonance system 200 having six shim coil loops arranged in a hexagonal arrangement. The system 200 includes an RF coil 202 and a shim coil array 204. The shim array 204 has six connected shim coils 210, 212, 214, 216, 218, and 220.

As with the system 100 in FIG. 1, the coil 202 has an outer circular shaped loop that represents a traditional RF-only loop coil with distributed capacitors 208. The shim coils 210, 212, 214, 216, 218, and 220 are diamond shaped loops each with a single RF choke 222. The shim coils 210, 212, 214, 216, 218, and 220 are coupled to a six-channel controller 230 through DC wires 232. The DC wires 232 include RF chokes 234. The number of RF chokes for each DC wire may be any positive integer. The diamond-shaped shim loops of the coils 210, 212, 214, 216, 218, and 220 are of identical sizes and are connected through five pairs of DC blocking capacitors 236 that are between 0-10,000 PF. The six shim coils 210, 212, 214, 216, 218, and 220 are arranged symmetrically relative to the RF coil 202 and routed sequentially in such a way that undesirable RF currents induced by the RF only coil 202 will flow along the path directed by the arrows. Therefore, the magnetic flux generated by RF currents have opposite signs (marks +–) in each pair of two adjacent shim coils and thus cancel each other. Thus the magnetic flux of the shim coils 210 and 216 cancel each other, the magnetic flux of the shim coils 212 and 218 cancel each other, and the magnetic flux of the shim coils 214 and 220 cancel each other. Each of the opposite flux coils cancel each other and thus, the magnetic flux of the shim coils 210 and 212 cancel each other, the magnetic flux of the shim coils 214 and 216 cancel each other, and the magnetic flux of the shim coils 218 and 220 cancel each other as well. The mutual inductance between the shim coil array 204 and the RF coil 202 is zero and the shim coil array 204 is thus inherently decoupled from the RF coil 202. The six shim coil arrangement in the system 200 allows for better shimming of the static B0 magnetic field. It is to be understood that the blocking capacitors 208 in series may be replaced by a single capacitor.

Figure 3A:
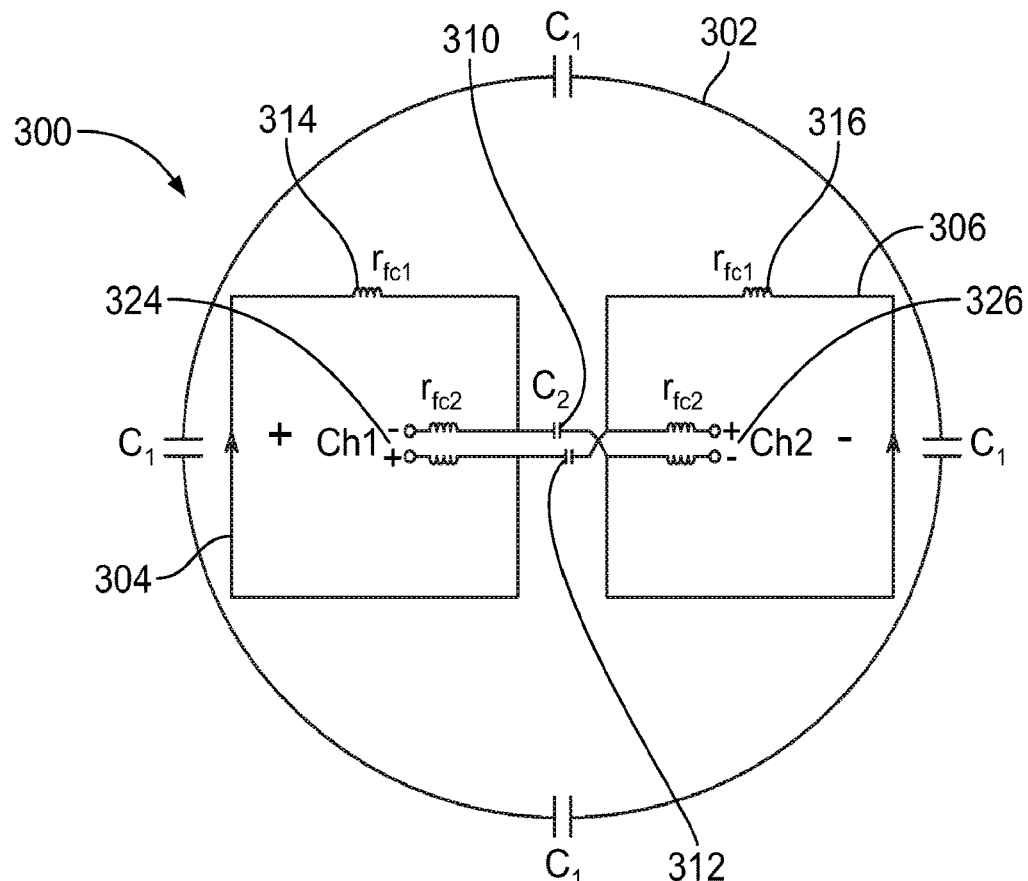
FIGS. 3A-3B are circuit diagrams of an example element design of a coil assembly with a separated RF coil and a shimming coil array with two coils.
Figure 3B:
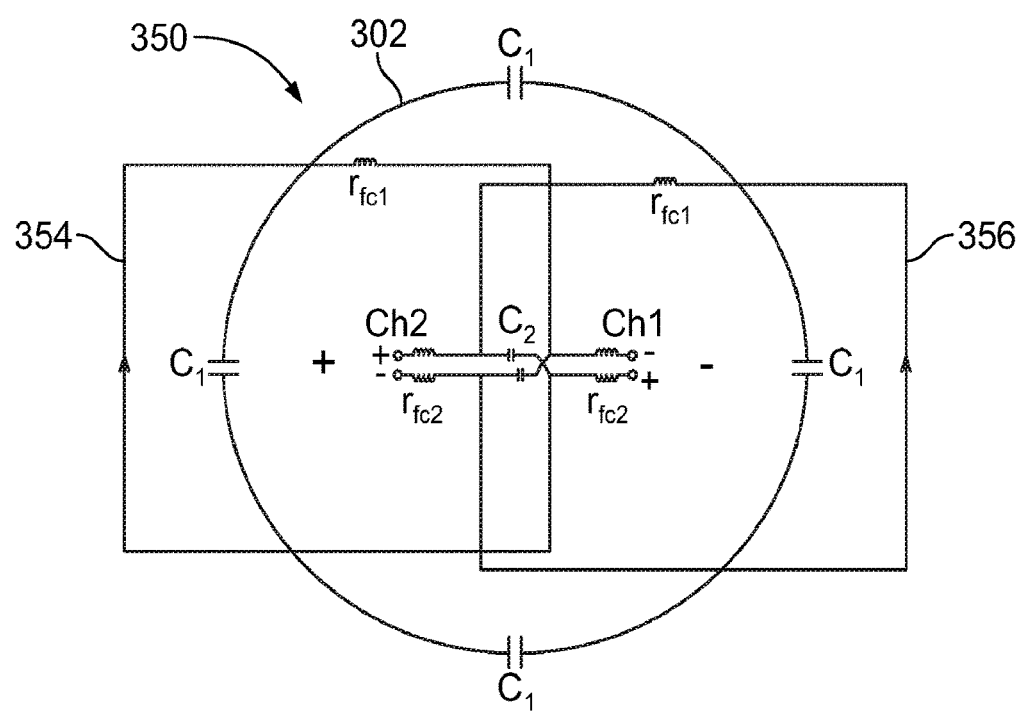

FIG. 3A shows a coil assembly 300 that is one example of a two-shim loop array. FIG. 3B shows another coil assembly 350 that is another example of a two-shim loop array. In both assemblies 300 and 350, the shim loops represent a two-channel shim loop that is controlled by a current controller with two channels.

The coil assembly 300 includes an RF coil 302. The circular shaped loop of the RF coil 302 represents a traditional RF-only loop coil. The coil assembly 300 includes two inner rectangular shim coils 304 and 306. The two shim coils 304 and 306 are connected through a pair of DC blocking capacitors 310 and 312 that may be between 0-10,000 PF. The shim coils 304 and 306 include respective RF chokes 314 and 316. A pair of DC current wires 324 and 326 each includes an RF choke and provides current to the respective shim coils 304 and 306. The number of RF chokes for each DC wire and shim coil may be any positive integer. The shim coils 304 and 306 are arranged symmetrically relative to the RF coil 302 so that undesirable RF currents induced by the RF only coil 302 flow along the path directed by the arrows. Therefore, the magnetic flux generated by RF currents have opposite signs (marks +–) in the two identical shim coils 304 and 306 and cancel each other. The mutual inductance between the two channel shim array of the shim coils 304 and 306 and the RF coil 302 is zero and the shim array is thus inherently decoupled from the RF coil 302.

Similarly, the coil assembly 350 includes an RF coil 352 and a two-channel shim array including a shim coil 354 and a shim coil 356. The two shim coils 354 and 356 are connected through a pair of DC block capacitors and each includes RF chokes. The two shim coils 354 and 356 are arranged to overlap each other and are partially outside the RF coil 352. Similar to the coil assembly 300, undesirable RF currents induced by the RF-only coil 352 flow along the path directed by the arrows. The magnetic flux generated by RF currents have opposite signs in the two identical shim coil 354 and 356 and cancel each other. The mutual inductance between the two channel shim array of the shim coil 354 and 356 and the RF coil 352 is zero and the shim array is thus inherently decoupled from the RF coil 302. The larger sized shim coils in FIG. 3B relative to those in FIG. 3A can generate a further shim field for the same DC current level while the smaller sized shim coils in FIG. 3A can generate a more localized shim field than the coils in FIG. 3B.

Figure 4A:
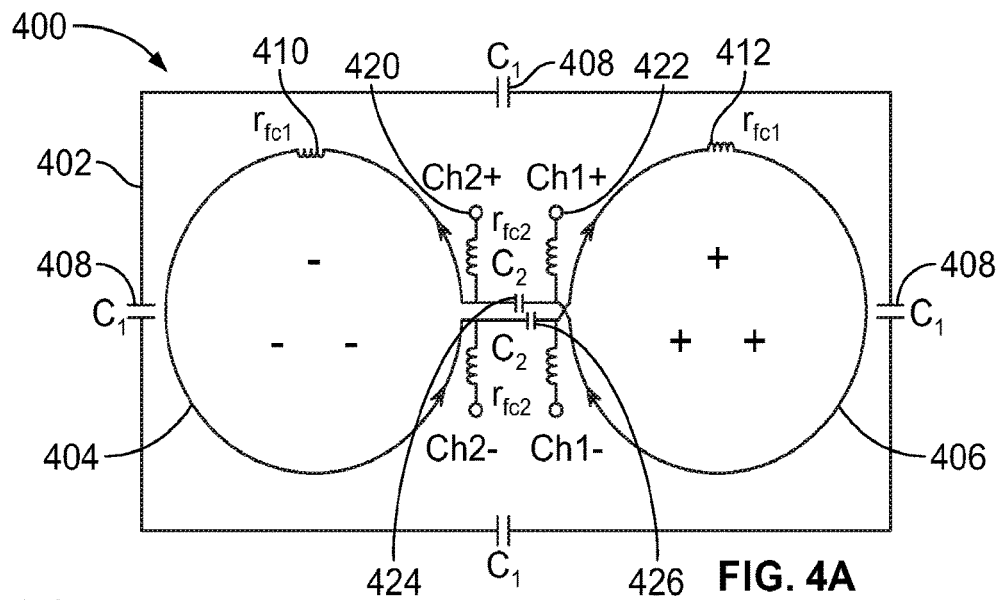
FIGS. 4A-4C are different alternatives of an example element design of a coil assembly with a rectangular loop RF coil separated from a shimming coil array with two coils.
Figure 4B:
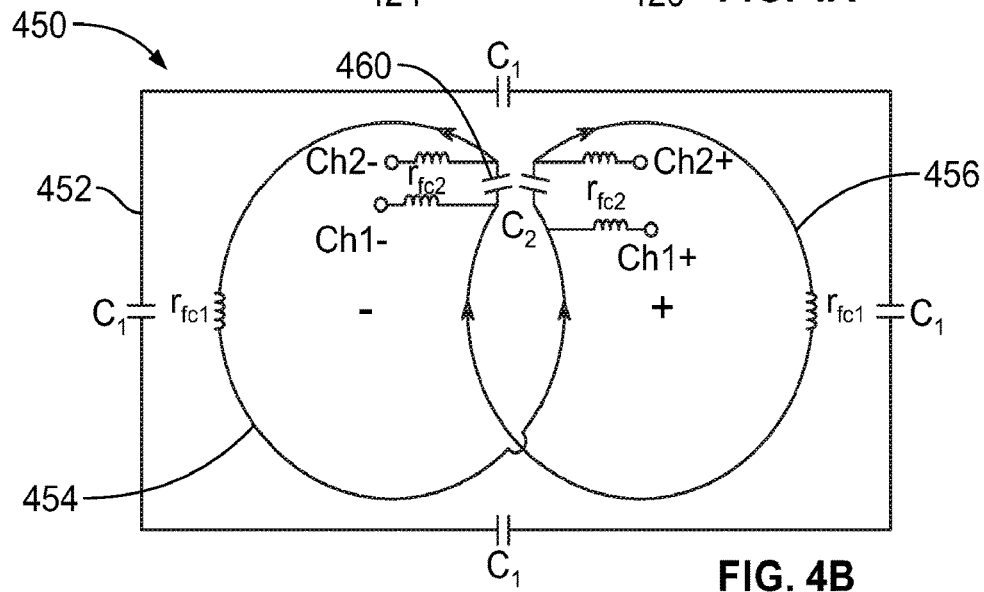
Figure 4C:
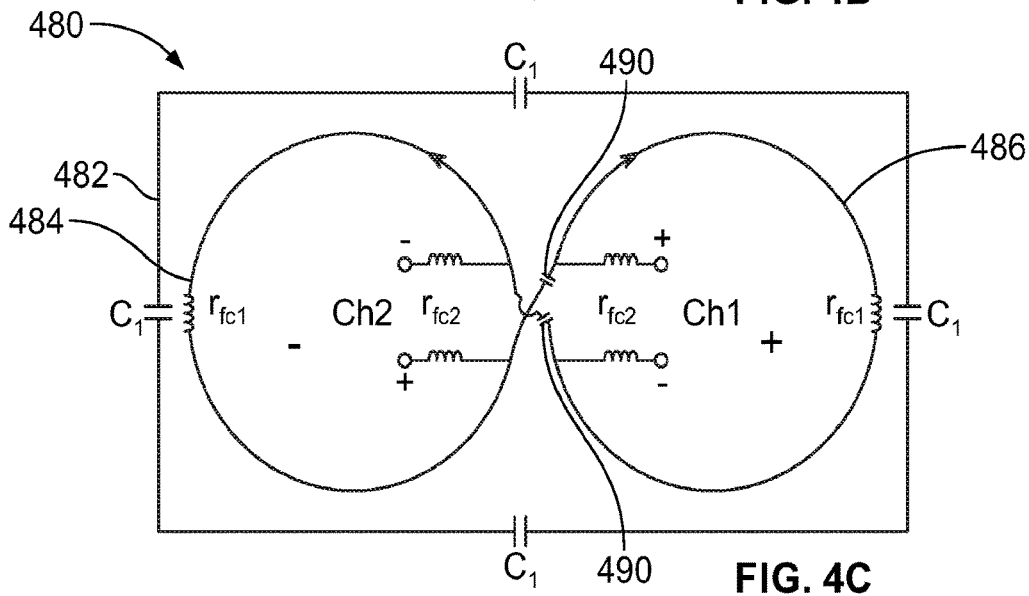

Additional variations of a shim array with two coils may have different shaped loops as shown in FIGS. 4A-4C. The coil assemblies in FIGS. 4A-4C show the flexibility both in the shape, size, and construction of the shim loops and the RF-only loop alike, and in their arrangements with respect to each other. FIG. 4A shows a coil assembly 400 having an RF coil 402 and a shim array having two shim coils 404 and 406. The RF coil 402 is a rectangular shaped loop and represents a traditional RF-only loop coil. The RF coil 402 includes several distributed capacitors 408. The two inner circular shaped shim coils 404 and 406 are of identical size and include RF chokes 410 and 412 respectively. The shim coils 404 and 406 are powered by respective channel input wires 420 and 422 that are controlled by a controller. The input wires 420 and 422 include RF chokes. The shim coils 404 and 406 are connected through a pair of DC blocking capacitors 424 and 426 that are 0-10,000 PF in this example. The positive terminal of the input wire 420 is coupled to the shim coil 404 and the blocking capacitor 424. The other end of the blocking capacitor 424 is coupled to the positive terminal of the input wire 422 and the shim coil 406. The negative terminal of the input wire 420 is coupled to the shim coil 404 and the blocking capacitor 426. The other end of the blocking capacitor 426 is coupled to the negative terminal of the input wires 422 and the shim coil 406.

The two shim coils 404 and 406 are arranged symmetrically relative to the RF coil 402 so that undesirable RF currents induced by the RF-only coil 402 will flow along the path directed by the arrows. Therefore, the magnetic flux generated by RF currents have opposite signs (marks +−) in the two identical shim coils 404 and 406 and cancel each other. The mutual inductance between the two shim coils 404 and 406 making up the two channel shim array and the RF coil 402 is zero and the shim array is thus inherently decoupled from the RF coil 402. The number of RF chokes for each shim loop and DC current wire may be any positive integer.

FIG. 4B shows a coil assembly 450 that is an alternate arrangement from the coil assembly 400 in FIG. 4A. The coil assembly 450 includes a rectangular RF-only coil 452 that surrounds two shim coils 454 and 456. The shim coils 454 and 456 are circular shaped and overlap each other. The shim coils 454 and 456 are powered by a controller and are coupled via blocking capacitors 460.

FIG. 4C shows a coil assembly 480 that is an alternate arrangement from the coil assembly 400 in FIG. 4A. The coil assembly 480 includes a rectangular RF-only coil 482 that surrounds two shim coils 484 and 486. The shim coils 484 and 486 are circular shaped and border each other. The shim coils 484 and 486 are powered by a controller and are coupled via blocking capacitors 490. FIGS. 4A-4C demonstrate that for a fixed size of the RF-only coil, the shim coil size may be larger for generating a further shim field as shown in FIG. 4B, or may be smaller for generating a more localized shim field as shown in FIG. 4A, or may be a medium size for a compromised shim field as in FIG. 4C in favor of different applications.

Figure 5A:
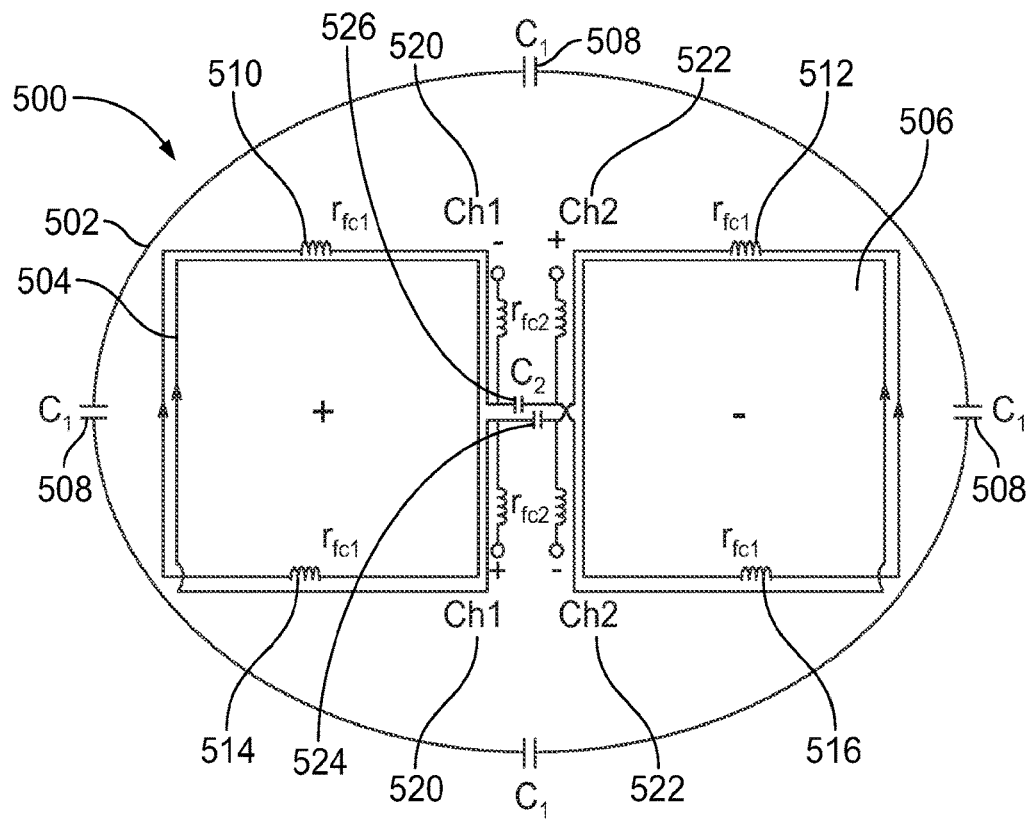
FIGS. 5A-5B are different alternatives of an example element design of a coil assembly with an RF coil separated from a shimming coil array with two coils, each with multiple loops.
Figure 5B:
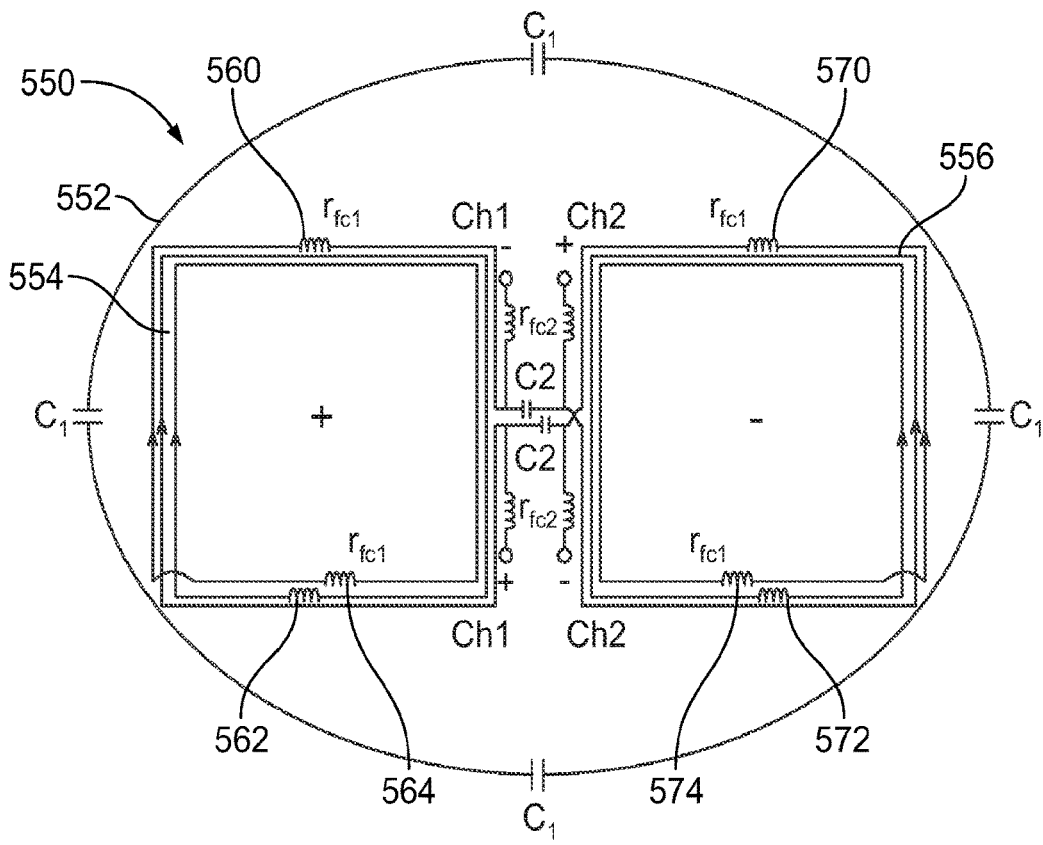

The shim array may also use multiple turn loops as shown in FIGS. 5A-5B. FIGS. 5A-5B show two possible alternatives to the two coil shim array shown in FIG. 3A. The coil assembly 500 has an RF coil 502 and a shim coil array having a shim coil 504 and a shim coil 506. The RF coil 502 includes several distributed capacitors 508. The two inner rectangular shaped shim coils 504 and 506 are of identical size. In this example, the shim coils 504 and 506 each have two turns or loops. The shim coils 504 and 506 each include a first loop having RF chokes 510 and 512 respectively. The second loop of each of the shim coils 504 and 506 also include a respective RF choke 514 and 516. The shim coils 504 and 506 are powered by respective channel input wires 520 and 522 that are controlled by a controller that regulates DC current supply to each channel. The input wires 520 and 522 include RF chokes. The shim coils 504 and 506 are connected through a pair of DC blocking capacitors 524 and 526 that are 0-10,000 PF in this example. For the shim coils 504 and 506, the two overlapped turns use insulated wires and are only electrically connected in series to the positive and negative terminals of the DC current supply via the input wires 520 and 522. The spacing between multiple shim loops is only for the demonstration purpose and in practice multiple turn wires are grouped with minimized spacing in between. The number of RF chokes for each shim loop and DC current wire may be any positive integer.

As previously explained, the two shim coils 504 and 506 are arranged symmetrically relative to the RF coil 502 so that undesirable RF currents induced by the RF-only coil 502 will flow along the path directed by the arrows. Therefore, the magnetic flux generated by RF currents have opposite signs (marks +−) in the two identical shim coils 504 and 506 and cancel each other. The mutual inductance between the two coils 504 and 506 making up the two channel shim array and the RF coil 502 is zero and the shim array is thus inherently decoupled from the RF coil 502. The two turn configuration of the shim coils 504 and 506 allows approximately half the current to generate the same shimming field strength as the shim loops in the other two shim loop configurations in FIGS. 3A-3B and 4A-4C.

Another example of a multiple turn shim coil system is the coil assembly 550 in FIG. 5B that includes three turn shim coils. The coil assembly 550 functions in the same manner as the coil assembly 500 in FIG. 5A. The coil assembly 550 has an RF coil 552 and a shim array having a shim coil 554 and a shim coil 556. The two inner rectangular shaped shim coils 554 and 556 are of identical size and have three turns each. Each of the turns include a RF choke such as RF chokes 560, 562, and 564 in the shim coil 554 and RF chokes 570, 572, and 574 in the shim coil 556. The three turns of each of the shim coils 544 and 556 are wired in series to the respective channel that supplies DC current. The three turn configuration of the shim coils 554 and 556 allows approximately a third of the current to generate the same shimming field strength as the shim loops in the other two shim loop configurations in FIGS. 3A-3B and 4A-4C. The number of RF chokes for each shim loop and DC current wire may be any positive integer.

Figure 5C:
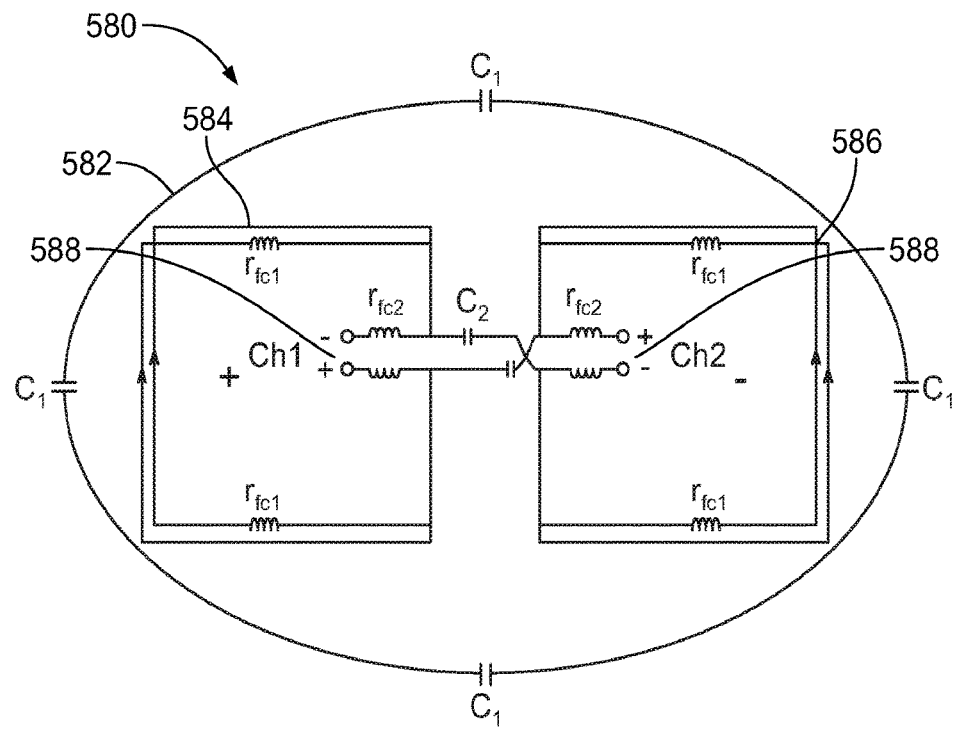
FIGS. 5C-5D are different alternatives of an example element design of a coil assembly with an RF coil separated from a shimming coil array with two coils, each with multiple loops and connected to a voltage source.

FIG. 5C is an alternate configuration of the double loop system shown in FIG. 5A. FIG. 5C shows an alternate coil assembly 580 that includes a circular RF coil 582 and two double loop shimming coils 584 and 586. In the alternate coil assembly 580, the double turns of the coils 584 and 586 are wired in parallel to one of the channels 588 connected to a voltage source. The channels 588 are wire pairs with a set of blocking capacitors arranged in a similar configuration as those in FIG. 5A.

Figure 5D:
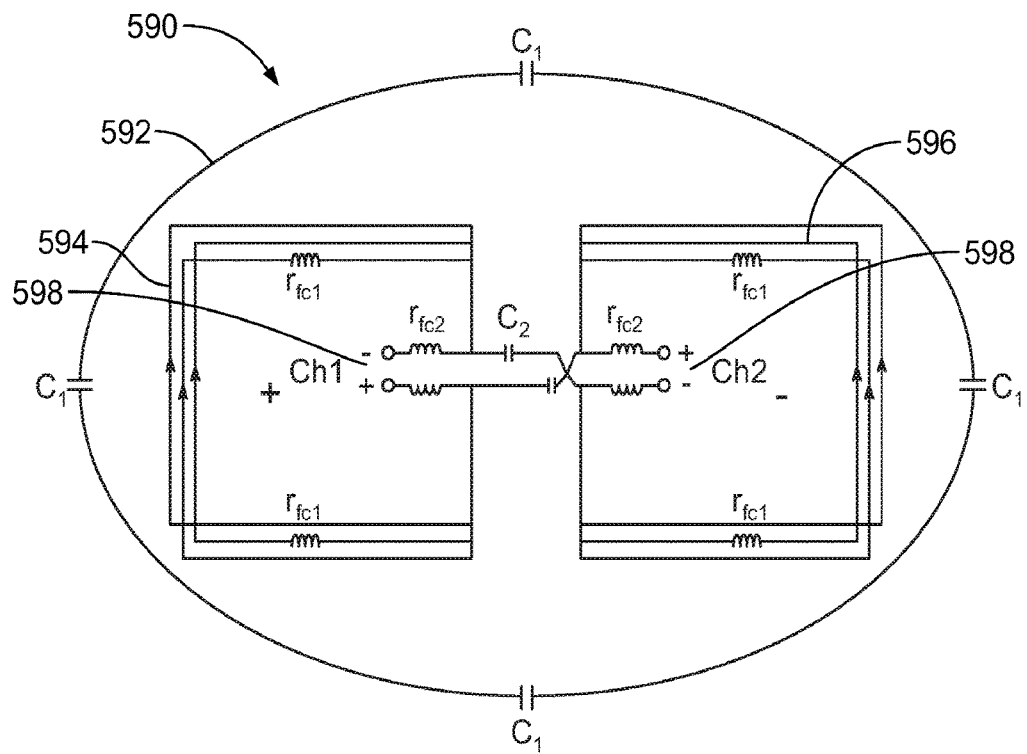

FIG. 5D is an alternate configuration of the double loop system shown in FIG. 5B. FIG. 5C shows an alternate coil assembly 590 that includes a circular RF coil 592 and two triple loop shimming coils 594 and 596. In the alternate coil assembly 590, the triple turns of the coils 594 and 596 are wired in parallel to one of the channels 598 connected to a voltage source. The channels 598 are wire pairs with a set of blocking capacitors arranged in a similar configuration as those in FIG. 5C.

All the shim loop configurations proposed in this disclosure may be extended to multiple turns such as two, three, or more turn loops. The multiple turns allow for decreased currents to produce the same shim fields as a single turn loop. Alternatively, the multiple turns allow for the same current level to produce a multiplied shim field strength compared to a single turn coil.

The number of the shim coils comprising an array alike can be 2, 4, 6, or any other positive even number. For example, the system 200 in FIG. 2 uses six connected shim coils while the systems in FIG. 3A and 3B and FIG. 4A, 4B, and 4C use two connected shim coils.

As long as these shim coils are arranged in a geometrical symmetry in relation to the respective RF loop coil, and are connected and routed sequentially in a way that unwanted RF currents induced by the RF loop coil generate magnetic flux of opposite polarities in each adjacent pair of two shim coil loops. 2N identical shim coil loops are sequentially connected through (2N-1) pair of DC blocking capacitors (where N is a positive integer). The total magnetic flux is thus zero or minimized. The mutual inductance between the separate shim coil array and the RF-only coil is thus zero or minimized. As a result, two completely separate shim and RF coil arrays are inherently decoupled from each other through this geometrical decoupling method as described above.

The size of identical shim loops may be larger or smaller than the RF loop. The relative positions between the separate shim coil array and RF loop can be flexible as long as it follows the abovementioned geometrical symmetry rule in order to zero or minimize the mutual inductance between two coil systems. For example, one half of the shim coil array can be outside the RF loop while the other half can be inside the RF loop but both coil systems can be still completely decoupled.

The shim coil array and RF-only coil are physically completely separate. They may share the same surface of a coil support structure. The wires comprising the shim array and the wires comprising the RF coil can cross each other with minimal distance but use insulated wires without electrical contact.

Figure 6:
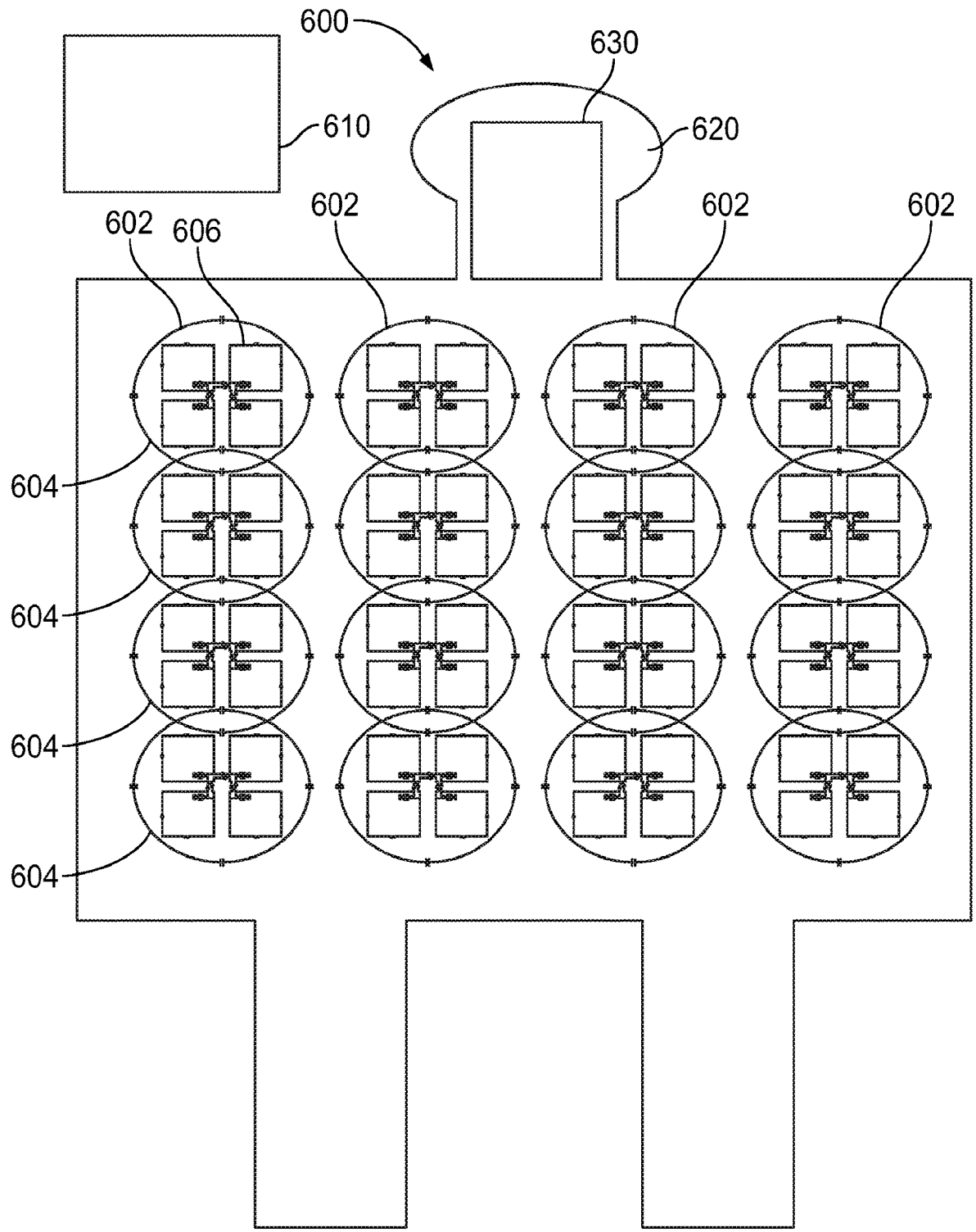
FIG. 6 is an example unified coil array system incorporating the coil assemblies having separated RF coils from the shimming coils.

FIG. 6 shows an example cardiac coil system 600 that includes an RF coil array composed of coil assemblies similar to the coil assembly 100 shown in FIG. 1. The cardiac coil system 600 may be used for magnetic resonance of a cardiac region of a patient. The cardiac coil system 600 includes sixteen coil assemblies 602 arranged in a four by four array. Each of the coil assemblies 602 includes a single RF loop 604 and a shimming array 606 having four shim coils. Thus, the coil system 600 has a sixteen channel RF coil array and a completely separate 64 channel shim array. Thus, each coil assembly 602 is a modular RF/shim element that includes one circular RF-loop overlapped with a four channel shim array, as described above in FIG. 1. A control unit 610 transmits RF signals to the RF coils of the coil assemblies 602 in transmit mode and receives the RF signals from each of the coil assemblies 602 in receive mode in conjunction with sensing of a cardiac region of a patient.

The 16 channel RF-only array in the system 600 has four gapped columns and each column contains four partially overlapped RF circular loops 604. The separate shim and RF arrays share the same surface of a coil support structure 620 with minimal physical distance but without electrical contact between each other. The DC current in each of the 64 shim loops is independently controlled by each channel of a 64 channel DC current supply 630.

Figure 7A:
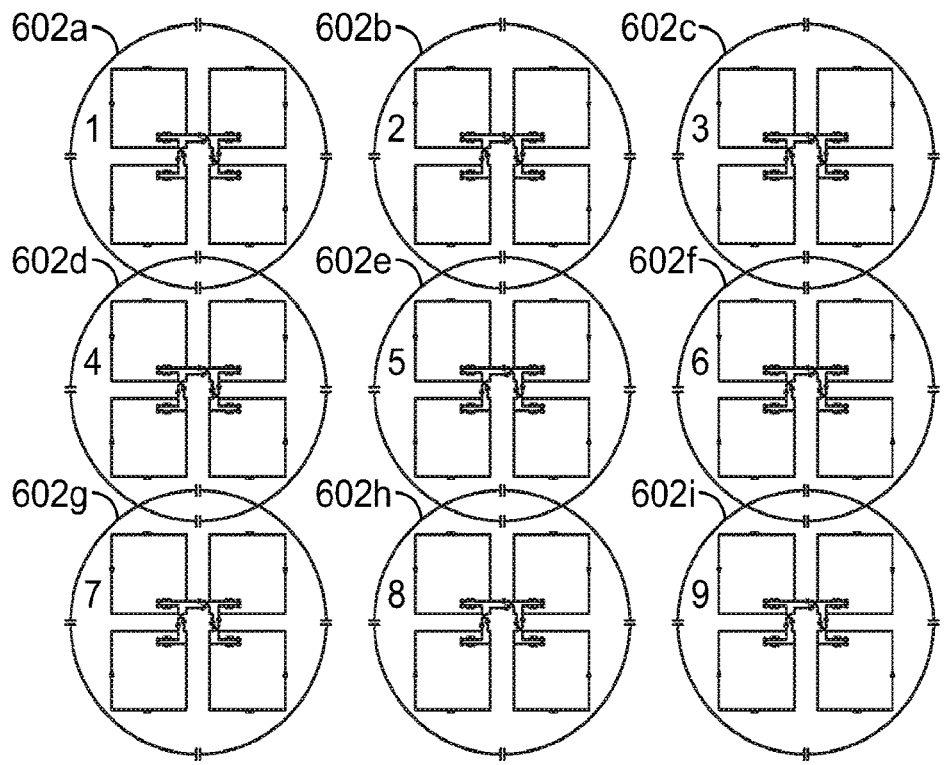
FIG. 7A is a close-up view of the coil assemblies in the unified coil array system shown in FIG. 6.

FIG. 7A is a magnified portion of the array 600 in FIG. 6 consisting of a 9 channel RF only array and a 36-channel shim array. In this example, the RF only array is part of nine coil assemblies 602a, 602b, 602c, 602d, 602e, 602f, 602g, 602h, and 602i that each have four shim coils.

Figure 7B:
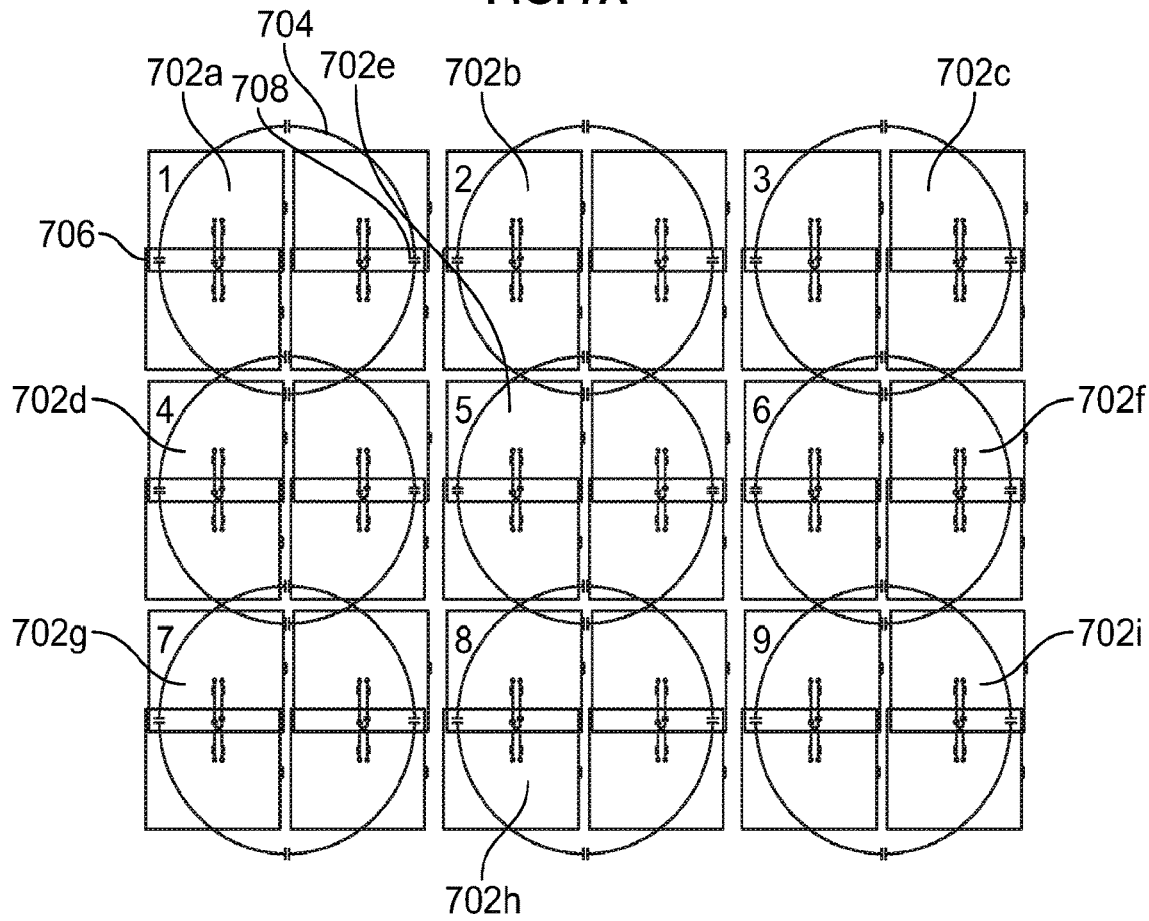
FIG. 7B is a close-up view of the use of coil assemblies having two separate two channel shim arrays in the unified coil array system shown in FIG. 6.

In comparison to FIG. 7A, FIG. 7B shows the substitution of a coil assembly array 700 similar to the modular RF/shim element design as described in FIG. 3B, in which a coil assembly array 702a includes one RF loop 704 is overlapped with two separate two channel shim arrays 706 and 708. The coil assembly 700 shows nine coil assemblies 702a, 702b, 702c, 702d, 702e, 702f, 702g, 702h, and 702i. It is apparent that all the RF/shim element designs illustrated in FIGS. 1-5 can be extended to formulate such a unified coil system.

The arrangement as shown in FIG. 7A, has a better decoupling effect between the shim array and RF array than the arrangement shown in FIG. 7B. For example, the four channel shim array within the coil assembly 602e element is completely decoupled from the RF loops in the assemblies 602b, 602d, 602e, 602f, and 602h due to geometrical symmetry to those assemblies. In contrast, the two channel shim arrays in the assembly 702e are only completely decoupled from the RF loops of the assemblies 702d, 702e, and 702f.

The assemblies described above, allow for the expansion of more shim loops than the number of available RF receivers resulting in increased shimming performance because of greater number of shimming loops. The resulting assemblies when used in an MRI system may greatly increase image fidelity and resolution, for example in fMRI of important brain regions prefrontal cortex and temporal cortex and in cardiac imaging of heart/lung boundaries.

The illustrated various geometrical decoupling methods provide a better decoupling between the shim arrays and the RF arrays causing a significantly increased signal-to-noise ratio (SNR) than iPRES designs. This is a considerably increased signal-to-noise ratio (SNR) at 3 Tesla, and significantly increased SNR at 7 Tesla, compared to iPRES designs with the same number of shim channels. The complexity in fabricating such a unified coil system is reduced because each shim loop only requires fewer RF chokes while each iPRES loop requires multiple RF chokes. This is particularly favorable for ultrahigh fields MRI scanners (e.g., 7 Tesla and above).

The assemblies described may be generally applied to coils for imaging all parts of a human or animal body, such as, for example, head coils, head neck spine coils, cardiac coils, body coils, torso coils, breast coils, musculoskeletal coils, knee coils, foot/ankle coils, carotid coils, wrist coils, and Cervical/Thoracic/Lumbar coils. The assemblies may also be applied to imaging non-tissue material including petroleum rock core, food, chemical system, and any other materials. The assemblies may be generally applied to all human or animal MRI scanners or even NMR spectrometers and can be generally applied to any main magnetic Bo field strengths, 1.5 T, 3 T, and 7 T. The assemblies may be applied to any MRI system equipped by any number of RF receivers.

The minimal requirement for the modification of MRI hardware architecture will make an easy transfer to next generation scanners. The add-on ability compared to a traditional RF array allows for upgrades as it does not require increase of radial or longitudinal dimensions of RF arrays and will look similar to a traditional coil and be used like a traditional coil after integrating the coil to the scanner.

The RF array may be a traditional RF coil/array, a receive-only coil/array, or a transmit-only coil/array, or a Transmit/Receive coil/array. It can be of any design, gapped or partially overlapped designs, or any other designs. The total number of RF receiver channels or DC shim channels in a unified coil system can be any positive integer, i.e., 1-4, 8, 16, 24, 32, 48, 64, 96, 128, 192, 256, and etc.

The shapes of each element shim loop and the RF loop can be any closed curve, any polygon, square, circular, rectangular, diamond, triangular, or any other shapes, and their sizes and positions can be flexible.

The coil assemblies described in FIGS. 1-5 may use previous designs including iPRES RF/DC shared loop modular design, RF/DC partially shared loop modular designs, or a traditional RF-only loop modular design without any integrated DC or B0 shim coils. In brief the unified coil array can be a mixture between the RF/shim element modular design in the above described assemblies and any other previous element modular designs.

Figure 8:
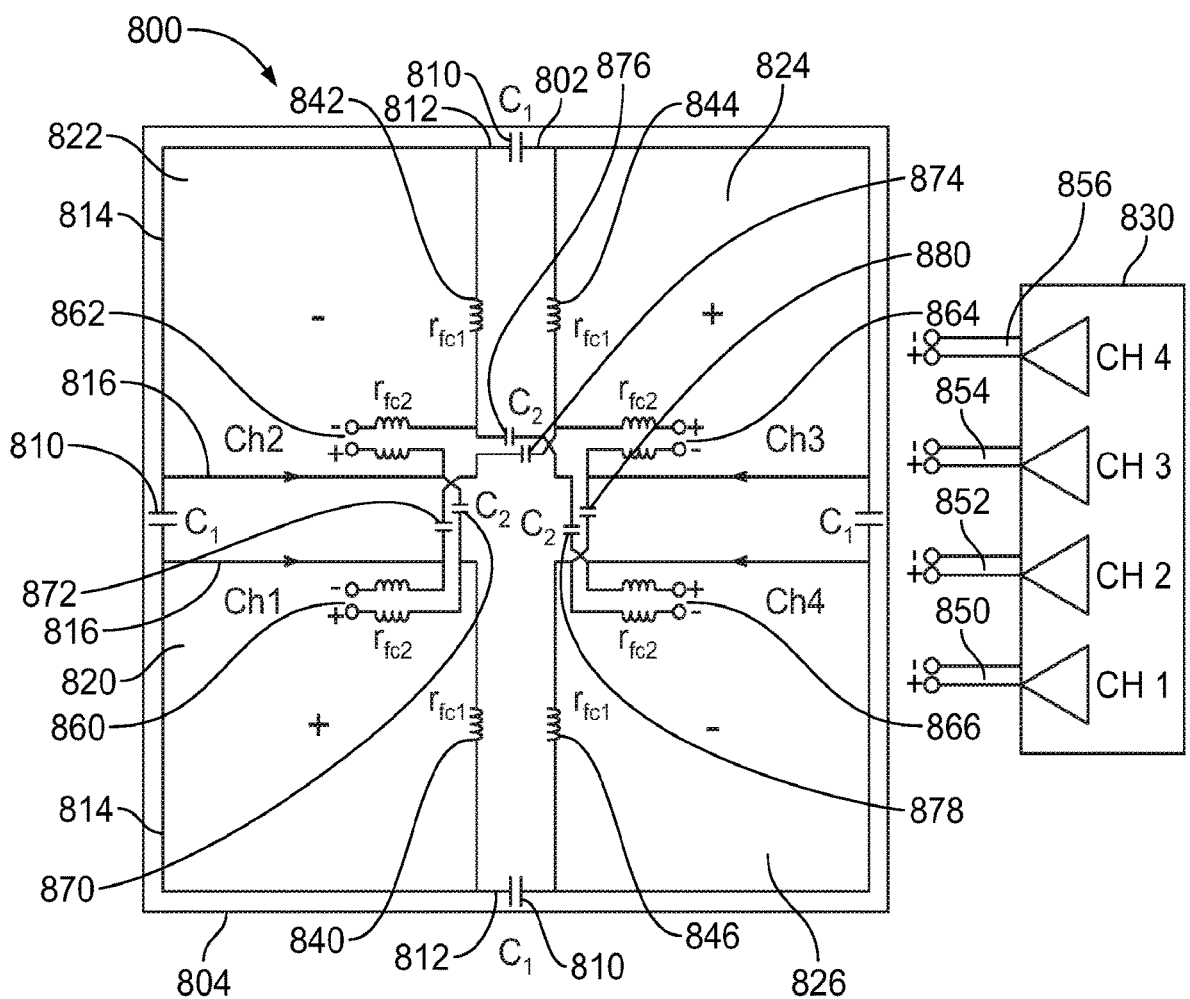
FIG. 8 is a circuit diagram of an example element design of a coil assembly with a partially separated RF coil and a shimming coil array sharing part of a common conductor.

FIG. 8 shows an alternate alternative coil assembly 800 having RF coil 802 and a shimming coil array that is a partially shared modular design. The RF coil 802 and the shimming coil array share at least one physical conductor, and are geometrically overlapped and share the same surface or layer of a mechanical supporting structure 804. The RF loop coil 802 is a large square shape loop including four capacitors 810. The capacitors 810 are wired on parts of a conductor wire 812 that is exclusively part of the RF coil 802. Other parts of the RF coil 802 such as the wires 814 are also part of the shim coils that make up the shimming coil array. The RF loop coil 802 either receives MR radiofrequency (RF) signals as a receive-only RF coil from the spins in tissue or non-tissue material, or transmits RF pulses as a transmit-only RF coil to excite the spins in tissue or non-tissue material, or performs both functions as being a transmit and receive RF coil.

The coil array 804 includes four sequentially-connected small square shape loops 820, 822, 824, and 826 of identical shape and size that represent one example of the respective shim coil array. The shim coil array 804 partially shares physically the same conductor/loop with four portions 814 of the outer RF loop coil 802. Other segments 816 of the coils of the shim coil array are unshared by the RF loop coil 802.

The four-channel shim coil array 804 is supplied with DC current through a DC current controller 830. The DC current of each shim coil 820, 822, 824, and 826 is independently controlled by one channel of the 4-channel DC current source amplifiers or supply in the DC current controller 830. Each inscribed square shim coil has at least one distributed RF chokes such as the RF chokes 840, 842, 844, and 846 distributed in the unshared portion 816 of each of the shim coils 820, 822, 824, and 826. The RF choke is an inductor in this example, but may be any other type of local RF choke circuits that prevent RF currents but allow DC currents to flow.

The channels Ch1+−, Ch2+−, Ch3+−, and Ch4+− in FIG. 1 represent the positive and negative polarities of DC current feeding terminals 850, 852, 854, and 856 of the 4-channel DC current source supply of the controller 130. The DC current for each shim coil 820, 822, 824, and 826 is independently controlled by each channel current amplifier in the controller 830 via respective pairs of DC feed wires 860, 862, 864, and 866. The current is controlled to all of the shim coils 820, 822, 824, and 826 via the controller 830 for a combined shim field. RF chokes are inserted in the DC feed wires 860, 862, 864, and 866 to eliminate unwanted RF currents. The RF chokes are inductors in this example, but may be other forms of local RF choke circuits for preventing RF currents but allowing DC currents. Each pair of DC feeding wires 860, 862, 864, and 866 are twisted together to avoid generating unwanted additional local magnetic fields. The number of RF chokes for each shim loop and DC current wire may be any positive integer.

The four identically sized square shim loops of the coils 820, 822, 824, and 826 are connected through three pairs of DC blocking capacitors 870, 872, 874, 876, 878, and 880. The positive terminal of the DC feed wire 860 is coupled to the shim coil 820 and the blocking capacitor 870. The other side of the blocking capacitor 870 is also coupled to the positive feed wire of the DC feed wire 862 and the shim coil 822. The negative terminal of the DC feed wire 860 is coupled to the shim coil 820 and the blocking capacitor 872. The other side of the blocking capacitor 872 is coupled to the blocking capacitor 874. The other side of the blocking capacitor 874 is coupled to the positive terminal of the DC feed wire 864 and the shim coil 824. The negative terminal of the DC feed wire 862 is coupled to the shim coil 822 and the blocking capacitor 876. The other side of the blocking capacitor 876 is also coupled to one side of the blocking capacitor 878. The other side of the blocking capacitor 878 is coupled to the positive feed wire of the DC feed wire 866 and the shim coil 826. The negative terminal of the DC feed wire 864 is coupled to the shim coil 824 and the blocking capacitor 880. The other side of the blocking capacitor 880 is coupled to the negative feed wire of the DC feed wire 866 and the shim coil 826. In this example, the capacitors 870, 872, 874, 876, 878, and 880 are between 0-10,000 PF.

As shown in FIG. 8, the four shim coils 820, 822, 824, and 826 are arranged symmetrically and routed sequentially in such a way that undesirable RF currents induced by the loop of the RF coil 802 will flow along the path directed by the arrows on the shimming coils 820, 822, 824, and 826. Therefore, the magnetic flux generated by RF currents have opposite signs (marks +− in FIG. 1) in each pair of two adjacent shim loops and thus cancel each other. For example, the loops 820 and 824 are positive flux while the loops 822 and 826 are negative flux. The mutual inductance between the shim coil array and the RF loop 802 is zero and the shim coil array is thus inherently decoupled from the RF coil 802. The geometrical symmetry of the shim coils 820, 822, 824, and 826 ensures that the direction of undesirable RF currents induced by the RF-only loop is clockwise in the shim coils 820 and 824 and is counterclockwise in the shim coils 822 and 826. Alternatively, if the direction of the undesirable current is counterclockwise in the shim coils 820 and 824, the direction is clockwise in the shim coils 822 and 826. As a result, the magnetic flux generated by the undesirable RF currents has opposite polarities in the shim coils 820 and 822 and 824 and 826, respectively.

The RF signals are only limited to flow in the outer large square loop 802 because various RF chokes 840, 842, 844, and 846 and the RF chokes in the wire pairs 860, 862, 864, and 866 prevent RF currents from leaking to the unshared portions of the DC shim coils 820, 822, 824, and 826.

Similarly, DC currents are only limited to flow in the inscribed four square shim coils 820, 822, 824, and 826 because the capacitors 810 block DC currents.

Figure 9:
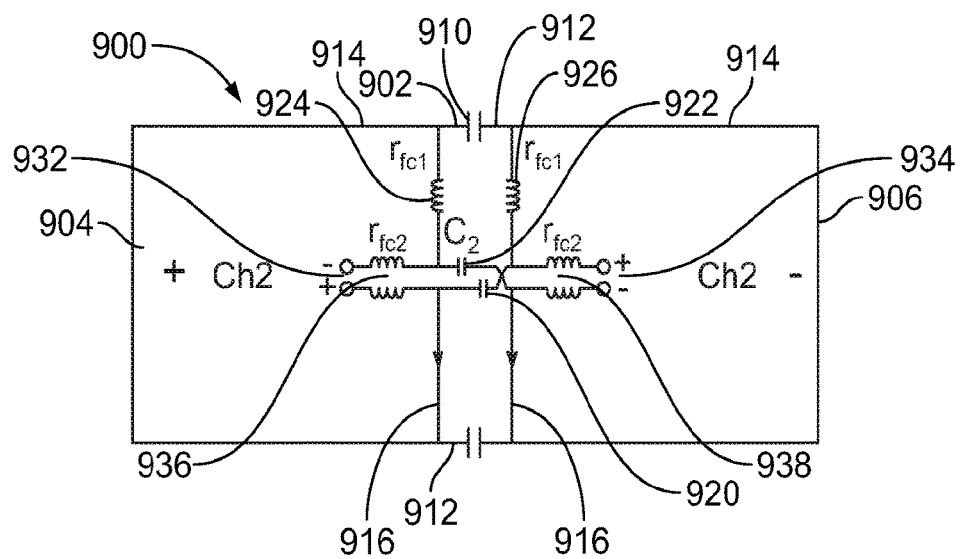
FIG. 9 is a circuit diagram of an example element design of a coil assembly with a partially separated RF coil and a shimming coil array with two coils sharing part of a common conductor.

FIG. 9 shows another example of a shim coil assembly 900 having an RF coil 902 and a shim array including two shim coils 904 and 906 where the shim coil array and RF coil have partially shared conductors. FIG. 9 shows the flexibility in the shim loops size and construction, and their arrangement with respect to the RF coil. The RF coil 902 includes a number of capacitors 910. In this example, the RF coil 902 includes segments 912 that are exclusively part of the RF coil 902. Other parts of the RF coil 902 such as the segments 914 are also part of the shim coils 904 and 906 that make up the shimming coil array. Other segments 916 of the shim coils 904 and 906 are not shared by the RF coil 902.

The two shim coils 904 and 906 are connected through a pair of DC blocking capacitors 920 and 922 that may be between 0-10,000 PF. The shim coils 904 and 906 include respective RF chokes 924 and 926. A pair of DC current wires 932 and 934 each include a pair of RF chokes 936 and 938 and provide current to the respective shim coils 904 and 906. The shim loops 904 and 906 are arranged symmetrically relative to the RF coil 902 so that undesirable RF currents induced by the RF-only coil 902 flow along the path directed by the arrows. Therefore, the magnetic flux generated by RF currents have opposite signs (marks +–) in the two identical shim coils 904 and 906 and cancel each other. The mutual inductance between the two channel shim array of the shim coils 904 and 906 and the RF coil 902 is zero and the shim array is thus inherently decoupled from the RF coil 902. The number of RF chokes for each shim loop and DC current wire may be any positive integer.

As shown in FIG. 9, the two square shim coils 904 and 906 partially shares physically the same conductor/loop with two portions 914 of the outer RF coil 902. The RF signal is only limited to flow in the outer square coil 902 because the RF chokes 924, 926, 936, and 938 prevent RF currents from leaking to the unshared portions of the DC current driven shim coils 904 and 906. Similarly, DC currents are limited to flow in each inscribed square coil 904 and 906 because of the capacitors 910 blocking DC currents.

As with the other examples herein, the shape of each shim coil and the RF loop coil may be a closed curve or a polygon including square, circular, rectangular, diamond, triangular, or any other shapes. The number of the inscribed shim loops comprising a shim array alike can be 2, 4, 6, or any other positive even number 2N.

As long as the shim coils are arranged in a geometrical symmetry in relation to the respective RF loop coil, and are connected and routed sequentially, unwanted RF currents induced by the RF loop coil generate magnetic flux of opposite polarities in each adjacent pair of two shim loops. The 2N identical shim loops are sequentially connected through (2N-1) pairs of DC blocking capacitors (where N is a positive integer). The total magnetic flux is thus zero or minimized. The mutual inductance between the shim coil array and the RF coil partially sharing a conductor is thus zero or minimized. As a result, two partially shared shim and RF coil arrays are inherently decoupled from each other through this geometrical decoupling method as described above. The size of the identical shim loops can vary. The relative positions between separate shim array and RF loop can be flexible as long as it follows the abovementioned geometrical symmetry rule in order to zero or minimize the mutual inductance between two coil systems.

Figure 10:
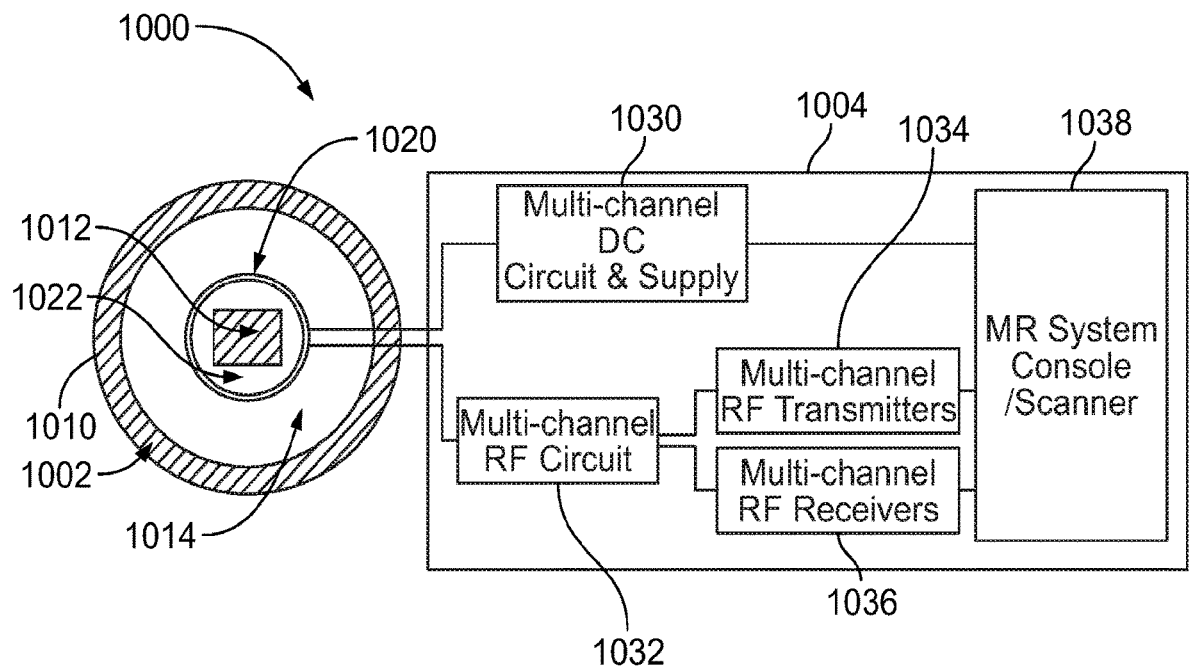
FIG. 10 is a block diagram of an MRI system that incorporates coil assemblies with separated or partially separated RF and shim coil arrays.

FIG. 10 is a Magnetic Resonance Imaging (MRI) system 1000. The system 1000 includes an MRI scanner 1002 that is controlled by an MRI control system 1004. In this example, MRI scanner 1002 includes a tubular supporting structure 1010 that surrounds a target object 1012 that may be a patient. The tubular supporting structure 1010 forms a bore 1014 that includes a permanent or superconducting (high-field magnet) that generates a static magnetic field (B0) of large magnitude such as 1.5 T, 3 T or 7 T. The target object 1012 is in proximity to a unified coil array system 1020 that is supported by a mechanical coil supporting structure 1020. The control system 1004 includes scanner operating components such as RF amplifiers, gradient amplifiers, controllers, and processors that typically direct the pulse sequences and select the scan planes of the target object 1012.

The unified coil array system 1020 may be composed of any of the coil assemblies described above such as the coil assemblies where the RF coil and shim coil arrays are separated as in FIGS. 1-5 or coil assemblies where the RF coil and shim coil arrays partially share conductor segments as shown in FIGS. 8A-8B. Thus, the unified coil array system 1020 may include an RF coil array having a plurality of coil elements where each of the coil elements are operative in an RF transmit mode or RF receive mode. The unified coil array system 1020 also includes a shim coil array having a plurality of coil elements operative in a direct current (DC) mode with DC current flow in the respective coil elements to generate local $B_0$ magnetic fields for $B_0$ shimming. The RF coil array and the shim coil array are geometrically overlapped and share the same surface or layer of the supporting structure 1022. The RF coil array and the shim coil array are decoupled by geometrical decoupling methods as above described to minimize the RF interaction between two coil systems.

The MRI control system 1004 includes a multi-channel DC circuit and current supply 1030, a multi-channel RF control circuit 1032, a multi-channel RF transmitter 1034, a multi-channel RF receiver 1036, and a control console 1038. As explained above, the DC circuit and current supply controller 1030 is in communication with the shim coil array of the united coil array system 1020 to supply DC current to the respective coil elements of the shim coil array. The DC controller 1030 includes a shim coil circuit that is in communication with the shim coil array configured to direct the DC power supply to supply DC current to the respective coil elements to generate the local $B_0$ magnetic fields for $B_0$ shimming. The DC controller 1030 allows separate control of each shim coil via separate channels.

The multi-channel RF control circuit 1032 is in communication with the RF coil array of the united coil array system 1020. The RF control circuit 1032 is configured to receive an MR signal from the target object 1012 via the multi-channel RF receiver 1036. The RF control circuit 1032 is also configured to transmit RF pulses to the target object 1012 from the multi-channel RF transmitter 1036.

The control console 1038 controls the multi-channel DC circuit and current supply 1030, the multi-channel RF control circuit 1032, the multi-channel RF transmitter 1034, the multi-channel RF receiver 1036 to transmit RF signals, adjust the shimming and receive RF signals in conjunction with the scanning function. Generally, the RF circuit controller 1032 is in communication with the MRI scanner 1002 to cause the RF coil array of the unified coil array system 1020 to transmit and receive while causing the shim coil array to shim a main field $B_0$ inhomogeneity using the generated local $B_0$ magnetic fields from the shim coil array. The multiple shimming coils allow the controller 1030 to be configured to generate the local $B_0$ magnetic fields to provide a uniform magnetic field across the target object 1012. This creates better imaging from the MRI scanner 1002. Other functions associated with the scanning process may also be performed. For example, the console 1038 may control shim coil circuit of the DC controller 1030 to generate $B_0$ maps associated with the generated local $B_0$ magnetic fields and perform $B_0$ shimming. The console 1038 may also control DC current in the coil elements of the shim coil array via the DC controller 1030 and measure the generated local $B_0$ magnetic fields.

Figure 11A:
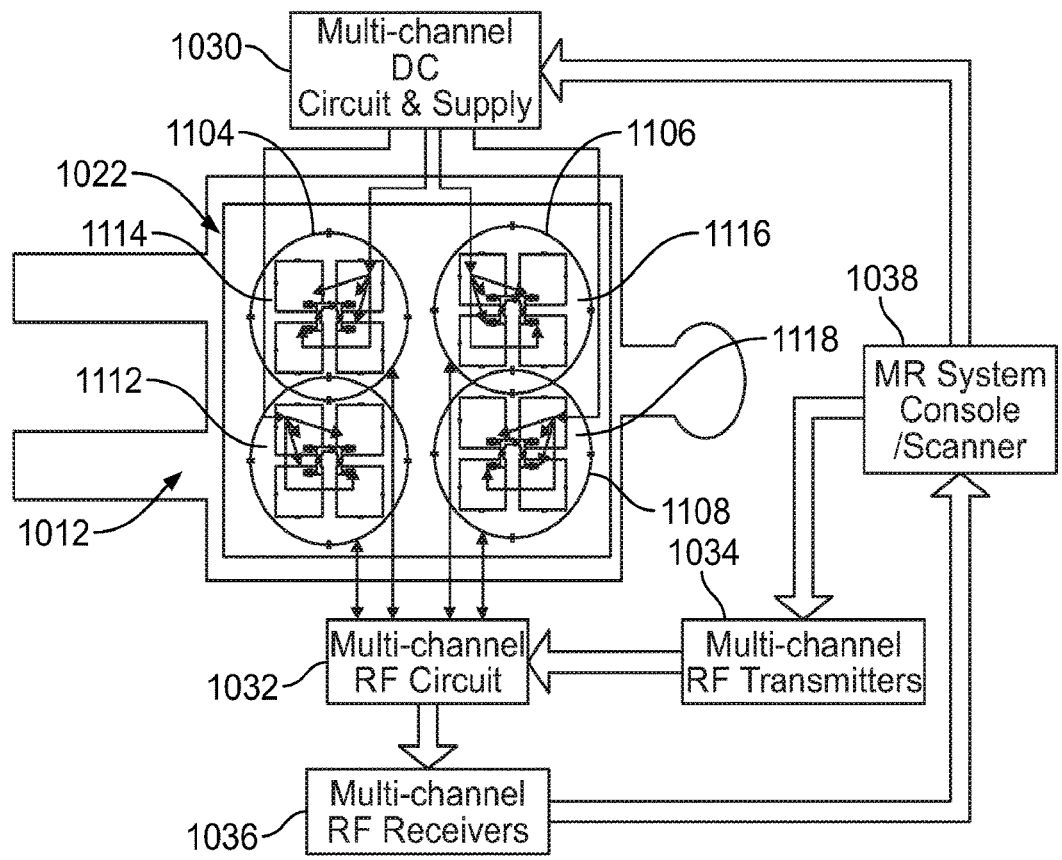
FIG. 11A is a block diagram of a unified coil array that has separate RF and shim coil arrays used in the MRI system in FIG. 10.

FIG. 11A shows a block diagram of the use of coil assemblies such as those shown in FIG. 1 as part of the unified coil array system 1020. In FIG. 11A, like elements are labeled with like numbers as in FIG. 10. As shown in FIG. 11A, the coil support structure 1020 allows placement of an RF coil array having four coil elements 1102, 1104, 1106, and 1108 in proximity to the target object 1012. As explained above, the RF coil elements 1102, 1104, 1106, and 1108 are coupled to the multi-channel RF circuit 1032 for receive and transmit modes. Each of the RF coil elements 1102, 1104, 1106, and 1108 are physically separated by symmetrically arranged shim coil arrays 1112, 1114, 1116, and 1118. The shim coil arrays 1112, 1114, 116, and 1118 in this example each have four shim coils. The shim coil arrays 1112, 1114, 1116, and 1118 are controlled for shimming by the DC controller 1030. The separate RF coil array and shim coil arrays 1112, 1114, 1116, and 1118 are geometrically overlapped and share the same surface or layer of the mechanical coil supporting structure 1022. In this example, since there are four RF coil elements 1102, 1104, 1106, and 1108, the RF control circuit is a four-channel circuit. Similarly, there are 16 shim coils in the four-shim coil arrays 1112, 1114, 1116, and 1118; the shim coils are controlled via a 16 channel DC controller such as the DC controller 1030. Of course more or less RF coils may be used and more or less shim coils may be used with corresponding control channels.

Figure 11B:
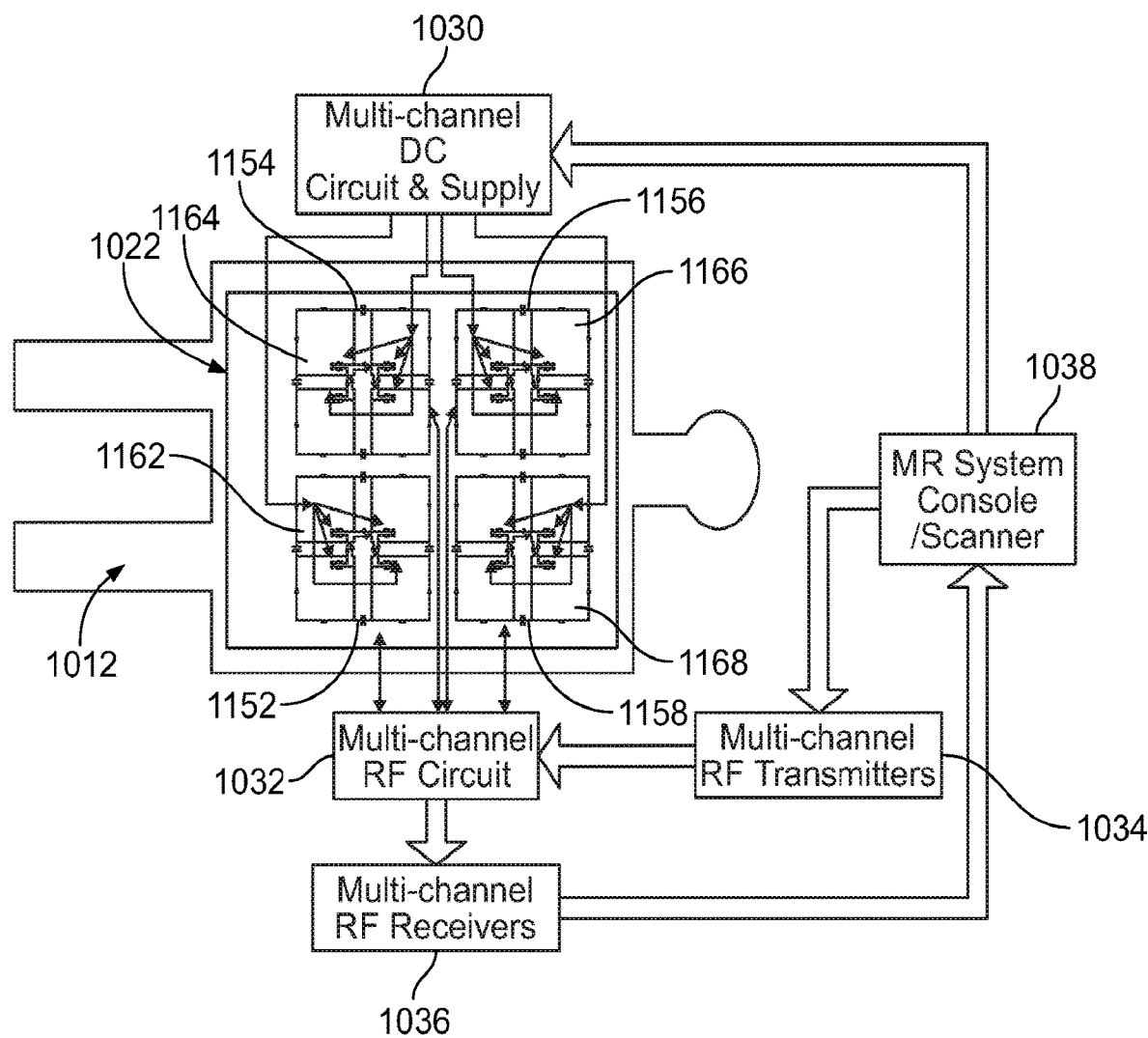
FIG. 11B is a block diagram of a unified coil array that has RF and shim coil arrays that share a common conductor used in the MRI system in FIG. 10.

FIG. 11B shows a block diagram of the use of coil assemblies such as those shown in FIG. 8 as part of the unified coil array system 1020. In FIG. 11B, like elements are labeled with like numbers as in FIG. 10. As shown in FIG. 11B, the coil support structure 1020 allows placement of an RF coil array having four coil elements 1152, 1154, 1156, and 1158 in proximity to the target object 1012. As explained above, the RF coil elements 1152, 1154, 1156, and 1158 are coupled to the multi-channel RF circuit 1032 for receive and transmit modes. Each of the RF coil elements 1152, 1104, 1156, and 1158 share at least one physical conductor with the shim coils or the respective symmetrically arranged shim coil arrays 1162, 1164, 1166, and 1168. The shim coil arrays 1162, 1164, 166, and 1168 in this example each have four shim coils. The shim coil arrays 1162, 1164, 1166, and 1168 are controlled for shimming by the DC controller 1030. The RF coil array and shim coil arrays 1162, 1164, 1166, and 1168 are geometrically overlapped and share the same surface or layer of the mechanical coil supporting structure 1022. In this example, since there are four RF coil elements 1152, 1154, 1156, and 1158, the RF control circuit is a four-channel circuit. Similarly, there are 16 shim coils in the four-shim coil arrays 1162, 1164, 1166, and 1168, and the shim coils are controlled via a 16 channel DC controller such as the DC controller 1030. Of course more or less RF coils may be used and more or less shim coils may be used with corresponding control channels.

The chokes throughout the above described examples may alternatively be an RF trap or filter using at least one inductor and at least one capacitor in parallel connection, with its resonant frequency adjusted and matched to the Larmor frequency of the MRI system. A low frequency AC power supply to supply a low frequency AC current may be used instead of the DC power supply for the shim coil arrays in the above examples.

The above examples may be applied to almost all MR coil systems including musculoskeletal coils with less receive channels (1-8), birdcage coils and even animal scanners, to meet various challenges in fMRI, DTI, MRSI and etc, and greatly improve image quality in air/tissue/bone interfaces from head to toe. Alternatively, the shim coils of the above examples may be replaced with gradient coils each having at least one coil element operative in a direct current (DC) or low frequency alternating current (AC) mode for spatial encoding of the spins to be imaged.

The above described UNIC systems are based on simple geometrical decoupling that may dramatically reduce RF interaction to almost negligible levels so that maximal SNR be maintained and RF chokes reduced to one per DC loop or even zero, an ideal solution for 7 T power MRI applications. Multiple turns largely increase shim field strengths for deep tissues shimming and 7 T MII systems, where higher shim field strengths are necessary.

FIG. 12 is a circuit diagram of an example united coil array 1200 that has a partially overlapped but separated RF and DC shim loops. The coil array 1200 includes an RF loop 1202 and a single circular loop shim coil 1204. The separate RF loop 1202 includes a number (1 to n) of distributed capacitors ($C_d$) 1210. The RF loop 1202 may also be an RF/DC shared-conductor loop as defined in the iPRES coils as described in WO 2014/003918 A1 hereby incorporated by reference.

The single circular loop shape DC shim coil 1204 is independently controlled by a DC current source supply channel 1220. The source supply channel 1220 has DC feeding terminals (Ch1+ and ch1− representing positive and negative polarities). An RF choke ($L_{c1}$) 1230 is inserted in each DC loop such as the DC shim coil 1204 to decouple from the transmit coil during RF excitation, and also to eliminate residual unwanted RF currents. The number of RF chokes per each DC shim loop may be zero to any integral numbers. One or more RF chokes ($L_{c2}$) 1232 are inserted in the DC feeding wires to eliminate unwanted RF currents. The number of RF chokes per DC-feeding wire can be zero to any integral numbers. A DC current blocking capacitor ($C_b$) 1234 is wired on the DC shim coil 1204. In this example, the DC current blocking capacitor 1234 has a value between 0-10,000 PF. Alternatively, the DC current blocking capacitor 1234 may be replaced by breaking the loop at the location of the capacitor 1234.

The separate RF and DC shim loops 1202 and 1204 are partially overlapped, as defined by a distance d shown in line 1240. The diameter of the DC shim loop 1204 may be defined as D. When the ratio d/D is a specific number between 0.7-0.8, the two loops 1202 and 1204 are completely decoupled. Using overlapping ratios of d/D=(0-0.5) can largely reduce coupling and using d/D=(0.5-0.75) can considerably reduce the coupling.

Figure 13:
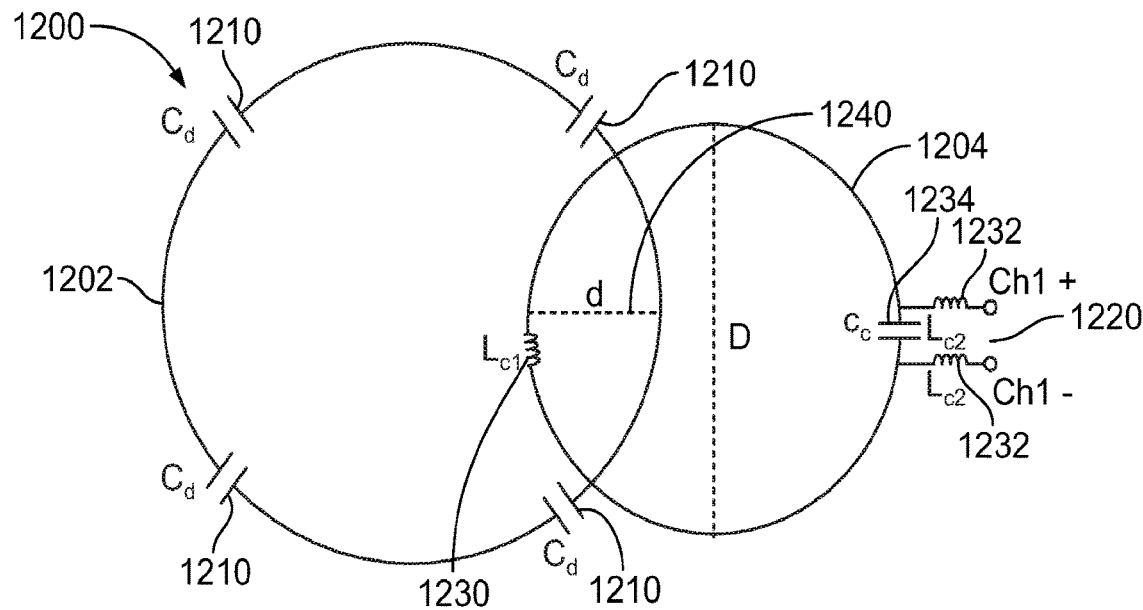
FIG. 13 is a circuit diagram of an example UNIC array for brain imaging.

Simple partial overlapping can largely reduce the strong coupling between two loops 1202 and 1204 so that fewer numbers of RF chokes are sufficient to eliminate the residual coupling. As illustrated in FIG. 13, the combination of a figure-8 shape shim loop decoupling and partial overlapping decoupling will allow the flexible arrangement of DC shim loops. The residual coupling will be eliminated or reduced to negligible levels by adding fewer RF chokes. Thus, the number of RF chokes for a circular DC loop can be zero, or more than one. Its shape may be rectangular, square, triangular, or any other shapes.

FIG. 13 shows an example UNIC array 1300 for brain imaging. The array 1300 includes seven large diameter loops 1302, 1304, 1306, 1308, 1310, 1312 and 1314 for RF reception. The loops 1302, 1304, 1306, 1308, 1310 and 1312 are RF/DC shared-conductor loops (iPRES designed loops according to the description in WO 2014/003918 A1, hereby incorporated by reference. The loop 1314 is an RF-only loop. The array 1300 includes four figure-8 shaped loops 1320, 1322, 1324 and 1326 that are separate shim loops targeting shimming of prefrontal cortex (PFC) or temporal lobes (TLs). The figure-8 shaped shim loops 1320, 1322, 1324, and 1326 (loops A B C and D) are inherently decoupled from both the RF-only loop 1314 and the RF/DC shared loops 1302, 1304, 1306, 1308, 1310, and 1312 as explained in reference to the above description of FIGS. 3-4 and largely decoupled from the loops 1304, 1306, 1308, and 1310 by partial-overlap decoupling as explained by the above description relating to FIG. 12. Residual RF coupling may be eliminated by at least one RF choke 1330.

Figure 14:
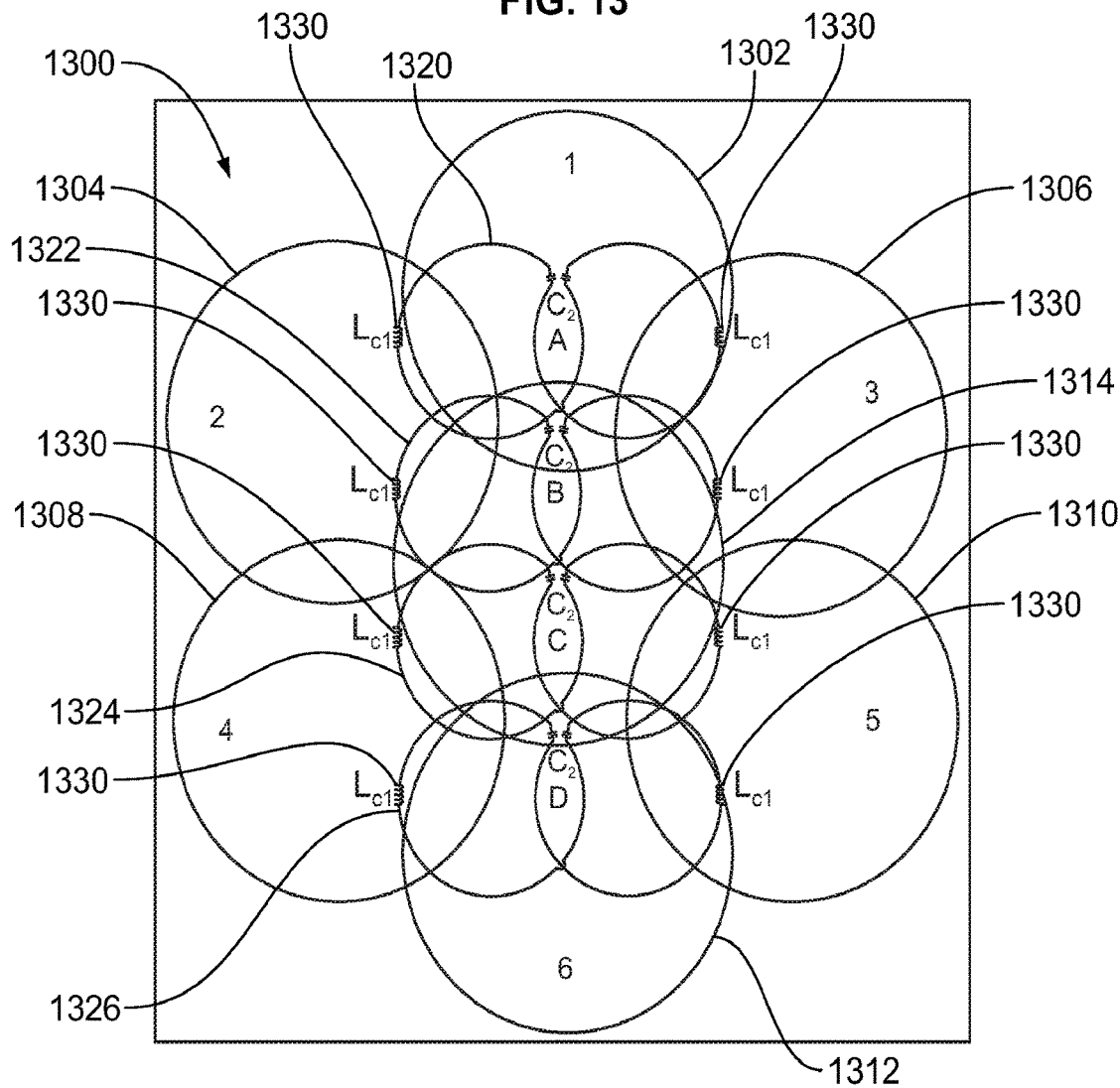
FIG. 14A is a UNIC head coil for brain imaging using the circuit in FIG. 13.
FIG. 14B are images that are the reulsts of a shimming simulation.
Figure 14A:
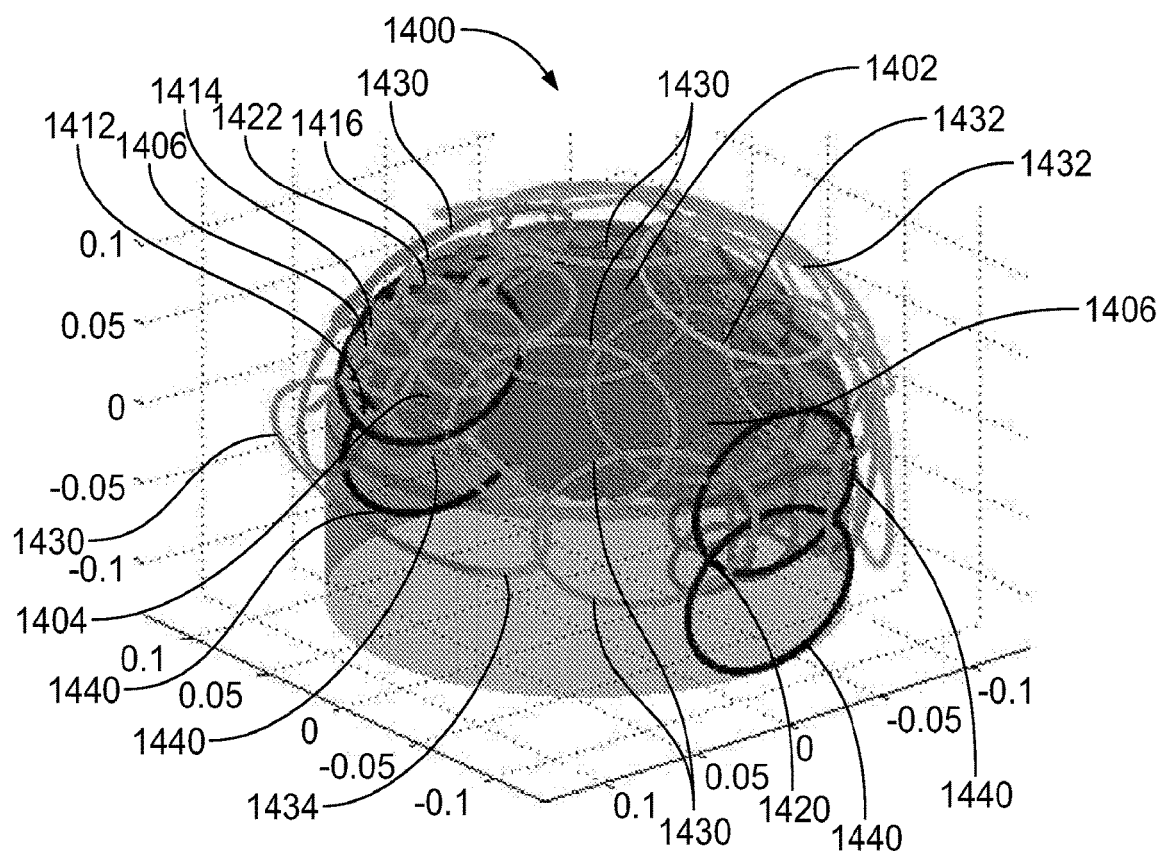

The whole head array is shown in FIG. 14A, where sizes of the figure-8 shim loops match those of anatomical structures. In addition, separate shim loops can enable multiple-turn, overcoming another major limit in shim field strength as iPRES loops are limited to a single turn only.

Alternatively, the RF-only loop 1314 can also be an iPRES RF/DC loop or red loops may also be RF-only loops. The four pairs of figure-8 shape shim-only loops 1320, 1322, 1324, and 1326 consist of eight independently controlled DC loops for Bo shimming. The DC feeding wires and current source supplies are not shown for simplicity of illustration in FIG. 13.

A practical example of using the array 1300 may be a brain fMRI coil. In such an application, four pairs of figure-8 shim-only loops may be placed as close as possible to the prefrontal cortex and each temporal lobe. The size may be matched to be 4-6 cm diameter of each circular DC loop for the PFC and 3-5 cm diameter of each circular DC loop for the temporal lobes. The nested large RF loops may be up to 32 channels for a scanner equipped by 32 channel RF receivers. The RF loops can be either RF-only loop such as the RF-only loop 1314 or an RF/DC iPRES type loop such as the loop 1302. The complexity is actually reduced because each DC loop only requires fewer RF chokes (0, 1, or n) while each iPRES loop requires 2-6 chokes. More importantly the shim-only loops effectively target the PFC and temporal lobe shimming.

The concepts of the brain application for the array in FIG. 13 may be generally applied to other coils for imaging other parts of human or animal body. The figure-8 shape may be any variety of shape. The number of pairs of figure-8 shim loops may be any integral number above 1. The size of the loops 1302, 1304, 1306, 1308, 1310, 1312 and 1314 may be any range of sizes. Single circular loops as that shown in FIG. 12 may be used rather than figure-8 shim loops.

FIG. 14A shows a UNIC head coil design 1400 for brain imaging under construction with 31-channel RF reception and 48-channel shimming, as described above with reference to FIG. 13. The coil design array 1400 is used for scanning a brain 1402 that includes a prefrontal cortex 1404 and temporal lobes 1406 of interest. Sizes of UNIC figure-8 shim loops match those of anatomical structures. In addition, separate shim loops may enable multiple-turn, overcoming another major limit in shim field strength as iPRES loops are limited to one turn only. A simulation shows about 80% reduction of standard deviation of field offsets for both the prefrontal cortex and temporal lobes. The simulation shows a UNIC head coil may reduce field inhomogeneity to an unprecedented level allowing application to a real whole brain imaging.

The UNIC head array 1400 includes three separate figure-8 shaped DC shim loops 1412, 1414, and 1416 at the prefrontal cortex. In this example the figure-8 shaped DC shim loops 1412, 1414 and 1416 are 5 cm in diameter. Two groups of four figure-8 shim loops 1420 and 1422 are located at each temporal lobe 1404. The loops in the groups of shim loops 1420 and 1422 are 4 cm in diameter in this example. The head array 1400 includes a group of eight iPRES loops 1430, a group of seventeen iPRES loops 1432 and a single IPRES loop 1434 that are arranged around the brain 1402 that perform RF reception and B0 shimming simultaneously. In this example the loops 1430, 1432 are 9.5 cm in diameter. The example head array 1400 also includes five RF-only loops 1440 that are in proximity to the prefrontal cortex 1402 and temporal lobes 1404.

Figure 14B:
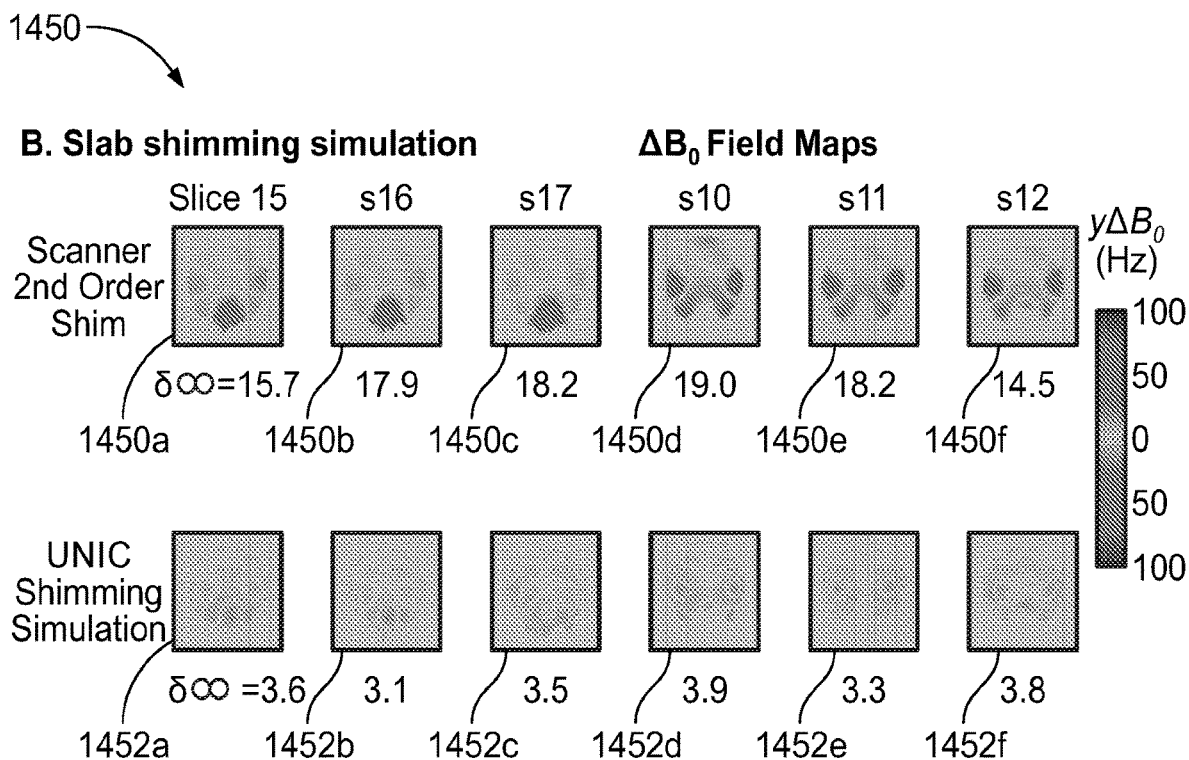

FIG. 14B shows the results of the shimming simulation. The first row are Bo field maps 1450a-1450f acquired on a 3T human scanner for a volunteer subject after applying the scanner to obtain second order global shimming. The second row are simulated Bo field maps 1430b-1450f after applying UNIC slab optimized shimming using the coil configure as in FIG. 14A. One slab has consecutive three 3-mm slices. After applying scanner second order spherical harmonic global shimming of the whole brain, the standard deviation of the field offsets within each slab of the subject brain is between 14.5-19 Hz, which were further reduced down to 3.1-3.9 Hz by further applying UNIC slab optimized shimming. The simulation results in FIG. 14B shows about 80% reduction of standard deviation of field offsets for both the prefrontal cortex and temporal lobes. The simulation shows a UNIC head coil can reduce field inhomogeneity to an unprecedented level, which may ultimately meet the challenge in fMRI for a real whole brain imaging.

Successful results have been obtained by bench measurements using a RF network analyzer to verify the elemental circuit design in FIG. 1. Without proposed geometrical decoupling, one and two shim loops, experienced dramatic drops in $Q_{Unloaded}/Q_{Loaded}$, to 70% and 46% compared to an RF-only loop. With UNIC designed loops, one turn figure-8 shim loop only dropped to 96% and had no drop in using critical overlapping decoupling. The UNIC butterfly shape design with 4-channel shim loops based on the circuit shown in FIG. 1, only had a Q-ratio drop of 94%. These results were obtained without any RF chokes.

Neighboring coupling was also negligible for UNIC one turn figure-8 shim loops. Two turn figure-8 shim loops and three turn figure-8 loops with 1-2 chokes per channel had slight drops of 92-93%. The UNIC loop has a better signal to noise ratio compared to iPRES loop while providing more shim channels and have less RF chokes per shim loop. Multiple-turn multiplies shim field strengths. UNIC coils don't increase coil assembly dimensions compared to traditional RF coils.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various examples known to the applicant at this time of filing the application has been presented and is intended for the purposes of illustration and description. The present description is not intended to be exhaustive nor limit the invention to the precise form disclosed and many modifications and variations are possible in the light of the above teachings. The examples described serve to explain the principles of the invention and its practical application and to enable others skilled in the art to utilize the invention in various examples and with various modifications as are suited to the particular use contemplated. Therefore, it is intended that the invention not be limited to the particular embodiments disclosed for carrying out the invention.

While particular examples of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A Magnetic Resonance Imaging (MRI) system, comprising:
    a unified coil array system including:
        a radio frequency (RF) coil array including a plurality of RF coil elements, the RF coil array being configured to operate operative in an RF mode for at least one of transmit or receive; and
        a separate shim coil array having a plurality of shim coil elements configured to operate in a direct current (DC) mode with direct current flow in the plurality of shim coil elements to generate one or more local B0 magnetic fields, the separate shim coil array being configured to operate independently from and simultaneously with the RF coil array to generate the one or more local B0 magnetic fields, the plurality of shim coil elements being physically separated from the plurality of RF coil elements,
        wherein each respective one of the plurality of RF coil elements in the RF coil array is associated with a respective 2N shim coil elements of the separate shim coil array,
        wherein at least part of each respective one of the plurality of RF coil elements overlaps with at least part of the respective 2N shim coil elements associated with the respective one of the plurality of RF coil elements,
        wherein each respective one of the plurality of RF coil elements is geometrically decoupled from the respective 2N shim coil elements associated with the respective one of the plurality of RF coil elements, and
        wherein each of the plurality of shim coil elements is physically arranged relative to each of the plurality of RF coil elements such that a mutual inductance between the plurality of shim coil elements and the plurality of RF coil elements is minimized or zero, thereby geometrically decoupling the plurality of shim coil elements from the plurality of RF coil elements;
    a magnet bore of a MRI scanner holding a target object, the RF coil element and the separate shim coil array positioned about the target object;
    a DC power supply in communication with the separate shim coil array to supply direct current to the at least one shim coil element of the separate shim coil array;
    a shim coil circuit in communication with the separate shim coil array configured to direct the DC power supply to supply the direct current to the at least one shim coil element to generate the one or more local B0 magnetic fields; and
    an RF circuit in communication with the RF coil element configured to receive an MR signal from the object for RF receive or transmit RF pulses to the object for RF transmit.

2. The system of claim 1, wherein a first one of the respective 2N shim coil elements has a magnetic flux of one polarity resulting from undesirable RF currents induced by the respective RF coil element, and a second one of the respective 2N shim coil elements has an opposite polarity induced by the same RF coil element.

3. The system of claim 1, wherein the 2N shim coil elements of each of the at least one of the plurality of RF coil elements are identical in size and shape, and at least two of the 2N shim coil elements are sequentially connected though a pair of DC blocking capacitors.

4. The system of claim 1, wherein the DC power source includes 2N channels, each of the channels corresponding to one of the plurality of shim coil elements and wherein the shim coil circuit allows individual adjustment of each direct current in each of the plurality of shim coil elements.

5. The system of claim 1, wherein at least one of the shim coil elements is a multiple-turn loop.

6. The system of claim 1, wherein the RF coil array is one of a receive-only RF coil array, a transmit-only RF coil array, or a transmit/receive RF coil array.

7. The system of claim 1, wherein the shape of at least one of the plurality of shim coil elements and at least one of the plurality of RF coil elements is a closed curve, a polygon, a circular shape, a square shape, a rectangular shape, a diamond shape, or a triangular shape.

8. The system of claim 1, wherein the unified coil array system is one of a head coil, a head neck spine coil, a cardiac coil, a body coil, a torso coil, a breast coil, a musculoskeletal coil, a knee coil, a foot/ankle coil, a carotid coil, a wrist coil, a Cervical/Thoracic/Lumbar coil.

9. The system of claim 1, wherein the MRI system images non-tissue material.

10. The system of claim 1, wherein the MM scanner is one of a human scanner, an animal scanner, a material MR system, or a NMR spectrometer.

11. The system of claim 1, wherein the unified coil array system includes a plurality of closely stacked layers of individually operable discrete RF coil elements of the RF coil array and shim coil elements of the separate shim coil array.

12. The system of claim 1, wherein the shim coil circuit is configured to use the generated one or more local B0 magnetic fields to perform B0 shimming.

13. The system of claim 1, wherein the shim coil circuit is configured to control the direct current in the at least one coil element of the separate shim coil array and measure the generated one or more local B0 magnetic fields.

14. The system of claim 1, wherein the shim coil circuit is in communication with an MR scanner, and wherein the at least one shim coil element in the separate shim coil array comprise at least one loop for direct current from the DC power supply, wherein the at least one loop includes an inductor.

15. The system of claim 1, wherein the RF coil array is a single transmit and receive RF coil array, and wherein the RF circuit is in communication with an MR scanner to cause the RF coil array to transmit and receive while causing the separate shim coil array to shim a main B0 field inhomogeneity using the generated one or more local B0 magnetic fields from the shim coil array.

16. The system of claim 1, wherein the separate shim coil array is configured to generate the one or more local B0 magnetic fields to provide a uniform B0 magnetic field across the target object.

17. The system of claim 1, wherein at least one of the plurality of RF coil elements shares at least one physical conductor with its associated 2N shim coil elements.

18. The system of claim 1, wherein the generated one or more local B0 magnetic fields are configured to be used for B0 shimming.

19. The system of claim 1, wherein the at least one shim coil element includes at least one circuit component having a resonant frequency that is generally equal to a Larmor frequency of the MRI system or within 10% of the Larmor frequency of the MRI system, the at least one circuit component including an inductor in parallel with a capacitor.

20. The system of claim 1, wherein a ratio of (i) an overlap distance between at least one of the plurality of RF coil elements and the respective 2N shim coil elements associated with the at least one of the plurality of RF coil elements to (ii) a diameter of its associated 2N shim coil elements is between about 0% and about 75%.

21. The system of claim 1, wherein the respective 2N shim coil elements associated with one of the plurality of RF coil elements includes a first shim coil element and a second shim coil element, the first shim coil element and the second shim coil element overlapping with each other, the first shim coil element and the second shim coil element both extending partially outside of the one of the plurality of RF coil elements.

22. The system of claim 1, wherein the respective 2N shim coil elements associated with one of the plurality of RF coil elements includes a first shim coil element and a second shim coil element, the first shim coil element and the second shim coil element being formed from a sequentially-routed single wire.

23. A method of operating a Magnetic Resonance (MR) system, comprising:
  providing at least one shim coil array with a shim coil element, the shim coil element having an associated circuit with a direct current (DC) current path comprising at least one loop;
  operating a radio frequency (RF) coil array including a plurality of RF coil elements in at least one of an RF transmit or receive mode, wherein the separate shim coil array is configured to operate independently from and simultaneously with the RF coil array to generate one or more local B0 magnetic fields, wherein the shim coil element is physically arranged relative to each of the plurality of RF coil elements such that a mutual inductance between the shim coil element and the plurality of RF coil elements is minimized or zero, thereby geometrically decoupling the shim coil element from the plurality of RF coil elements, and wherein each of the plurality of RF coil elements in the RF coil array is associated with a respective 2N shim coil elements of the at least one shim coil array;
  flowing direct current through the DC current paths of the shim coil element of the at least one shim coil array concurrently with the transmit or receive mode of the RF coil array; and
  generating the one or more local B0 magnetic fields in response to the flow of the direct current through the DC current paths of the shim coil element.

24. The method of claim 23, wherein the total magnetic flux from the at least one shim coil array is minimized.

25. The method of claim 23, wherein at least one of the plurality of RF coil elements shares at least one physical conductor with its associated 2N shim coil elements.

26. The method of claim 23, wherein the generated one or more local B0 magnet fields are used to shim an imaging space of a magnet of the MR system.

27. A unified coil array assembly for a Magnetic Resonance Imaging (MRI) system, comprising:
  a radio frequency (RF) coil array including a plurality of RF coil elements; and
  at least one shim coil array with a plurality of shim coil elements, each of the plurality of shim coil elements being physically separated from the RF coil array, each of the plurality of RF coil elements being associated with a respective 2N shim coil elements of the at least one shim at least one shim coil array,
  wherein each of the plurality of shim coil elements includes a direct current (DC) current loop having a DC power supply connection with positive and negative terminals, and wherein direct current flows and circulates in the DC current loop to generate one or more local B0 magnetic fields,
  wherein the unified coil array assembly is configured to simultaneously provide an RF mode for at least one of transmit or receive and a direct current mode to generate the one or more local B0 magnetic fields,
  wherein each of the plurality of shim coil elements is physically arranged relative to each of the plurality of RF coil elements such that a mutual inductance between the plurality of shim coil elements and the plurality of RF coil elements is minimized or zero, thereby geometrically decoupling the plurality of shim coil elements from the plurality of RF coil elements, and
  wherein the separate shim coil array is configured to operate independently from and simultaneously with the RF coil array to generate the one or more local B0 magnetic fields.

28. The unified coil array assembly of claim 27, wherein each of the plurality of shim coil elements include an RF choke.

29. The unified coil array assembly of claim 27, wherein a first RF choke is wired in series between the positive terminal and the DC current loop and a second RF choke is wired in series between the negative terminal and the DC current loop.

30. The unified coil array assembly of claim 27, wherein at least one of the plurality of shim coil elements has a first segment shared with one of the plurality of RF coil elements and a second segment not shared with the one of the plurality of RF coil elements.

31. The unified coil array assembly of claim 27, wherein the generated one or more local B0 magnetic fields are configured to be used for B0 shimming.

32. The system of claim 1, wherein a distance between at least one of the plurality of RF coil elements and the respective 2N shim coil elements associated with the at least one of the plurality of RF coil elements is minimized, and wherein (i) the distance between the at least one of the plurality of RF coil elements and the respective 2N shim coil elements associated with the at least one of the plurality of RF coil elements is approximately zero such that least a portion of the at least one of the plurality of RF coil elements and the respective 2N shim coil elements associated with the at least one of the plurality of RF coil elements are physically touching, (ii) the distance between the at least one of the plurality of RF coil elements and the respective 2N shim coil elements associated with the at least one of the plurality of RF coil elements is between about 0 millimeters and about 10 millimeters, (iii) wherein the at least one of the plurality of RF coil elements and the respective 2N shim coil elements associated with the at least one of the plurality of RF coil elements are positioned in the same layer of a mechanical holding structure of the system, or (iv) the distance between the at least one of the plurality of RF coil elements and the respective 2N shim coil elements associated with the at least one of the plurality of RF coil elements is between about 0 millimeters and about 300 millimeters.

33. A Magnetic Resonance Imaging (MRI) system, comprising:
- a unified coil array system including:
    - a radio frequency (RF) coil element configured to operate in an RF mode for at least one of transmit or receive; and
    - a separate shim coil array having at least one shim coil element configured to operate in a direct current (DC) mode with direct current flow in the at least one shim coil element to generate one or more local B0 magnetic fields, the at least one shim coil element being configured to operate independently from and simultaneously with the RF coil array to generate the one or more local B0 magnetic fields, the plurality of shim coil elements being physically separated from the plurality of RF coil elements;
    - wherein at least part of the RF coil element overlaps with at least part of the separate shim coil array, and
    - wherein the at least one shim coil element is physically arranged relative to the RF coil element such that a mutual inductance between the at least one shim coil element and the RF coil element is zero, thereby geometrically decoupling the at least one shim coil element from the RF coil element
- a magnet bore of a MRI scanner holding a target object, the RF coil element and the separate shim coil array positioned about the target object;
- a DC power supply in communication with the separate shim coil array to supply direct current to the at least one shim coil element of the separate shim coil array;
- a shim coil circuit in communication with the separate shim coil array configured to direct the DC power supply to supply the direct current to the at least one shim coil element to generate the one or more local B0 magnetic fields; and
- an RF circuit in communication with the RF coil element configured to receive an MR signal from the object for RF receive or transmit RF pulses to the object for RF transmit.

\* \* \* \* \*